United States Patent
Kurek et al.

(10) Patent No.: US 12,011,507 B2
(45) Date of Patent: Jun. 18, 2024

(54) MRNA DELIVERY COMPOSITION

(71) Applicant: NanoVation Therapeutics Inc., Vancouver (CA)

(72) Inventors: Daniel Kurek, Vancouver (CA); Anthony Tam, Vancouver (CA); Maunish Barvalia, Vancouver (CA); Dominik Witzigmann, Vancouver (CA); Jayesh Kulkarni, Vancouver (CA)

(73) Assignee: NanoVation Therapeutics Inc., Vancouver (CA)

( * ) Notice: Subject to any disclaimer, the term of this patent is extended or adjusted under 35 U.S.C. 154(b) by 0 days.

(21) Appl. No.: 18/194,084

(22) Filed: Mar. 31, 2023

(65) Prior Publication Data

US 2023/0398082 A1 Dec. 14, 2023

Related U.S. Application Data

(60) Provisional application No. 63/362,345, filed on Apr. 1, 2022.

(51) Int. Cl.
*A61K 9/51* (2006.01)
*A61K 9/00* (2006.01)
(Continued)

(52) U.S. Cl.
CPC .......... *A61K 9/5123* (2013.01); *A61K 9/0019* (2013.01); *A61K 48/0041* (2013.01); *C12N 15/88* (2013.01)

(58) Field of Classification Search
CPC ... A61K 9/0019; A61K 48/0041; C12N 15/88
See application file for complete search history.

(56) References Cited

U.S. PATENT DOCUMENTS

| 7,514,099 B2 | 4/2009 | Chen et al. |
| 7,901,708 B2 | 3/2011 | Maclachlan et al. |

(Continued)

FOREIGN PATENT DOCUMENTS

| CA | 1337332 C | 10/1995 |
| CA | 2731173 A1 | 2/2010 |

(Continued)

OTHER PUBLICATIONS

Meng et al., Nanoplatforms for mRNA Therapeutics, Adv Therap., pp. 1-23 (Year: 2020).*

(Continued)

*Primary Examiner* — Carlos A Azpuru
(74) *Attorney, Agent, or Firm* — Knobbe Martens Olson & Bear LLP

(57) ABSTRACT

The present disclosure provides a lipid nanoparticle for extrahepatic delivery of mRNA, the lipid nanoparticle comprising: (i) mRNA cargo; (ii) a phosphatidylcholine lipid content of from mol % to 70 mol %; (iii) a ionizable, cationic lipid content of from 5 mol % to 50 mol %; (iv) a sterol selected from cholesterol or a derivative thereof; and (v) a hydrophilic polymer-lipid conjugate that is present at a lipid content of 0.5 mol % to 5 mol. Further provided is a lipid nanoparticle preparation comprising lipid nanoparticles having encapsulated mRNA and 20 to mol % of a phosphatidylcholine lipid, an ionizable lipid; and at least one of a sterol and a hydrophilic polymer-lipid conjugate, the lipid nanoparticles exhibiting at least a 10% increase in gene expression of the mRNA in vivo as measured in one or more extrahepatic organs or tissues. The lipid nanoparticles have an electron dense region and a nitrogen-to-phosphate charge ratio of between 4 and 15.

30 Claims, 25 Drawing Sheets

(51) Int. Cl.
A61K 48/00 (2006.01)
C12N 15/88 (2006.01)

(56) References Cited

U.S. PATENT DOCUMENTS

| | | |
|---|---|---|
| 8,058,069 B2 | 11/2011 | Yaworski et al. |
| 8,492,359 B2 | 7/2013 | Yaworski et al. |
| 8,822,668 B2 | 9/2014 | Yaworski et al. |
| 9,301,923 B2 | 4/2016 | Baryza et al. |
| 9,364,435 B2 | 6/2016 | Yaworski et al. |
| 9,504,651 B2 | 11/2016 | Maclachlan et al. |
| 9,878,042 B2 | 1/2018 | Yaworski et al. |
| 10,703,789 B2 | 7/2020 | Fougerolles et al. |
| 10,772,975 B2 | 9/2020 | Bancel et al. |
| 10,898,574 B2 | 1/2021 | Fougerolles et al. |
| 11,141,378 B2 | 10/2021 | Yaworski et al. |
| 11,191,849 B2 | 12/2021 | Abrams et al. |
| 11,219,634 B2 | 1/2022 | Prieve et al. |
| 11,229,609 B2 | 1/2022 | Cheng et al. |
| 11,291,734 B2 | 4/2022 | Guild et al. |
| 11,338,044 B2 | 5/2022 | Guild et al. |
| 11,547,764 B2 | 1/2023 | Guild et al. |
| 11,564,998 B2 | 1/2023 | Fougerolles et al. |
| 2006/0051405 A1 | 3/2006 | Maclachlan et al. |
| 2006/0240554 A1 | 10/2006 | Chen et al. |
| 2011/0111044 A1 | 5/2011 | Zhao et al. |
| 2012/0308663 A1 | 12/2012 | Roger et al. |
| 2015/0140069 A1 | 5/2015 | Hong et al. |
| 2019/0314291 A1 | 10/2019 | Besin et al. |
| 2020/0078313 A1 | 3/2020 | Roy et al. |
| 2020/0129445 A1 | 4/2020 | Patel et al. |
| 2021/0145982 A1 | 5/2021 | Hoge et al. |
| 2021/0267895 A1 | 9/2021 | Yaworski et al. |
| 2021/0346306 A1 | 11/2021 | Dimitrov et al. |
| 2022/0071916 A1 | 3/2022 | Cheng et al. |
| 2022/0218614 A1 | 7/2022 | Ali et al. |

FOREIGN PATENT DOCUMENTS

| | | | |
|---|---|---|---|
| CA | 2764832 A1 | 12/2010 | |
| CA | 2486007 * | 11/2011 | |
| CA | 2486007 C | 11/2011 | |
| CA | 2740000 C | 12/2017 | |
| CA | 3103528 A1 | 12/2019 | |
| CA | 3111483 A1 | 3/2020 | |
| WO | 2019067992 A1 | 4/2019 | |
| WO | 2019089828 A1 | 5/2019 | |
| WO | 2020051223 * | 3/2020 | |
| WO | 2020051223 A1 | 3/2020 | |
| WO | 2020072324 A1 | 4/2020 | |
| WO | 2022011156 A1 | 1/2022 | |
| WO | 2022251953 * | 12/2022 | A61K 9/51 |
| WO | WO 2022/251953 | 12/2022 | |
| WO | WO 2022/251959 | 12/2022 | |
| WO | WO2022251953 A1 † | 12/2022 | |

OTHER PUBLICATIONS

Ambegia et al., "Stabilized plasma-lipid particles containing PEG-diacylglycerols exhibit extended circulation lifetimes and tumor selective gene expression", Biochimica et Biophysica Acta, 2005, 1669:155-163.

Brockerhoff and Ramsammy, "Preparation and Structural Studies of Cholesterol Bilayers", Biochimica et Biophysica Acta, 1982, 691:227-232.

Buse and El-Aneed, "Properties, engineering and applications of lipid-based nanoparticle drug-delivery systems: current research and advances", Nanomedicine, 2010, 5(8): 1237-1260.

Cheng and Lee, "The role of helper lipids in lipid nanoparticles (LNPs) designed for oligonucleotide delivery", Advanced Drug Delivery Reviews, 2016, 99:129-137.

Cheng et al., "Selective Organ Targeting (SORT) nanoparticles for tissue specific mRNA delivery and CRISPR/Cas gene editing", Nat. Nanotechnol., Apr. 2020, 15(4): 313-320.

Dabkowska et al., "The effect of neutral helper lipids on the structure of cationic lipid monolayers", J. R. Soc. Interface, 2012, 9:548-561.

Drummond et al., "Optimizing Liposomes for Delivery of Chemotherapeutic Agents to Solid Tumors", Pharmacological Reviews, 1999, 51(4):691-743.

Evers et al., "State-of-the-Art Design and Rapid Mixing Production Techniques of Lipid Nanoparticles for Nucleic Acid Delivery", Nucleic Acid Delivery, Small Methods, 2018, 2:1700375.

Fenton et al., "Customizable lipid nanoparticle materials for the delivery of siRNAs and mRNAs", Angew. Chem. Int. Ed., 2018, 57:13582-13586.

Foglia et al., "Structural Studies of the Monolayers and Bilayers Formed by a Novel Cholesterol-Phospholipid Chimera", Langmuir, 2011, 27:8275-8281.

Han et al., "An ionizable lipid toolbox for RNA delivery", Nature Communications, 2021, 12:7233.

Hayes et al., "Genospheres: self-assembling nucleic acid-lipid nanoparticles suitable for targeted gene delivery", Gene Therapy, 2006, 13:646-651.

Hecker et al., "Non-Viral DNA and mRNA Gene Delivery to the CNS Pre-Operatively for Neuroprotection and Following Neurotrauma", Molecular Therapy, 2004, 9(1):S258.

Hess et al., Vaccination with mRNAs encoding tumor-associated antigens and granulocyte-macrophage colony-stimulating factor efficiently primes CTL responses, but is insufficient to overcome tolerance to a model tumor/self antigen, Cancer Immunol. Immunother., 2006, 55:672-683.

Iman et al., "Characterization of the colloidal properties, in vitro antifungal activity, antileishmanial activity and toxicity in mice of a distagmasterylhemisuccinoyl-glycero-phosphocholine liposome-intercalated amphotericin B", International Journal of Pharmaceutics, 2011, 408:163-172.

Jeffs et al., "A scalable, extrusion-free method for efficient liposomal encapsulation of plasmid DNA", Pharmaceutical Research, 2005, 22(3):362-372.

Kauffman et al., "Optimization of Lipid Nanoparticle Formulations for mRNA Delivery in Vivo with Fractional Factorial and Definitive Screening Designs", Nano Lett, 2015, 15(11):7300-7306.

Koynova and Tenchov, "Recent Patents on Cationic Lipid Carriers for Delivery of Nucleic Acid", Recent Patents on DNA & Gene Sequences, 2011, 5:8-27.

Kubota et al., "Effect of the nanoformulation of siRNA-lipid assemblies on their cellular uptake and immune stimulation", International Journal of Nanomedicine, 2017, 12:5121-5133.

Kulkarni et al., "Lipid nanoparticles enabling gene therapies: from concepts to clinical utility", Nucleic Acid Therapeutics, 2018, 28(3):146-157.

Kulkarni et al., "On the Formation and Morphology of Lipid Nanoparticles Containing Ionizable Cationic Lipids and siRNA", ACS Nano, 2018, 12:4787-4795.

Kulkarni et al., "On the role of helper lipids in lipid nanoparticle formulations of siRNA", Nanoscale, 2019, 11:21733-21739.

Leung et al., "Microfluidic mixing: a general method for encapsulating macromolecules in lipid nanoparticle structures", The Journal of Physical Chemistry, 2015, 119:8698-8607.

Leung, "Biophysical characterization of lipid nanoparticles containing nucleic acid polymers as produced by microfluidic mixing", A Thesis Submitted in Partial Fulfillment of the Requirements for Degree of Doctor of Philosophy of the Faculty of Graduate and Postdoctoral Studies, the University of British Columbia, Aug. 2014, copyright Alex Kar Kei Leung.

Martinon, "Induction of virus-specific cytotoxic T lymphocytes in vivo by liposome-entrapped mRNA", Eur. J. Immunol., 1993, 23:1719-1722.

Mochizuki et al., "The role of the helper lipid dioleoylphosphatidylethanolamine (DOPE) for DNA transfection cooperating with a cationic lipid bearing ethylenediamine", Biochimica et Biophysica Acta, 2013, 1828:412-418.

Mockey et al., "mRNA-based cancer vaccine: prevention of B16 melanoma progression and metastasis by systemic Injection of MART1 mRNA histidylated lipoplexes", Cancer Gene Therapy, 2007, 14:802-814.

(56) References Cited

OTHER PUBLICATIONS

Ordobadi, "Lipid nanoparticles for delivery of bioactive molecules", A Thesis submitted in partial fulfillment of the requirements for the degree of doctor of philosophy in The Faculty of Graduate and Postdoctoral Studies (Biochemistry and Molecular Biology) at the University of British Columbia, Vancouver, British Columbia, Nov. 2019.

Pascola, "Vaccination with Messenger RNA (mRNA)", Toll-like Receptors (TLRs) and Innate Immunity, In Handbook of Experimental Pharmacology, Eds. S. Bauer and G. Hartmann, Springer-Verlag Berlin Heidelberg, 2008, 183:221-235.

Patel et al., "Naturally occurring cholesterol analogues in lipid nanoparticles induce polymorphic shape and enhance Intracellular delivery of mRNA", Nature Communications, 2020, 11(1):3435.

PCT Written Opinion and Search Report of the Canadian Intellectual Property Office acting as the International Searching Authority, PCT international application No. PCT/CA2023/050439, dated May 26, 2023.

Pozzi et al., "Transfection efficiency boost of cholesterol-containing lipoplexes", Biochimica et Biophysica Acta, 2012, 1818:2335-2343.

Roces et al., "Manufacturing considerations for the development of lipid nanoparticles using microfluidics", Pharmaceutics, 2020, 12:1095.

Sakurai et al., "Effects of erythrocytes and serum proteins on lung accumulation of lipoplexes containing cholesterol or DOPE as a helper lipid in the single-pass rat lung perfusion system", European Journal of Pharmaceutics and Biopharmaceutics, 2001, 52:165-172.

Sato et al., "Hydrophobic scaffolds of pH-sensitive cationic lipids contribute to miscibility with phospholipids and improve the efficiency of delivering short interfering RNA by small-sized lipid nanoparticles", Acta Biomaterialia, 2020, 102:341-350.

Shoenmaker et al., "mRNA lipid nanoparticle COVID-19 vaccines: structure and stability", International Journal of Pharmaceutics, 2021, 601:120586.

Su et al., "In Vitro and In Vivo mRNA Delivery Using Lipid-Enveloped pH-Responsive Polymer Nanoparticles", Molecular Pharmaceutics, 2011, 8:774-787.

Tam et al., "Stabilized plasmid-lipid particles for systemic gene therapy", Gene Therapy, 2000, 7:1867-1874.

Tenchov et al., "Cubic Phases in Phosphatidylcholine-cholesterol mixtures: Cholesterol as Membrane 'Fusogen'", Biophysical Journal, 2006, 91:2508-2516.

Yamamoto et al., "Current prospects for mRNA delivery", European Journal of Pharmaceutics and Biopharmaceutics, 2009, 71:484-489.

Yoshioka et al., "Cationic liposomes-mediated plasmid DNA delivery in murine hepatitis induced by carbon tetrachloride", Journal of Liposome Research, 2009, 19(2):141-147.

Yuan et al., "Ternary nanoparticles of anionic lipid nanoparticles/ protamine/DNA for gene delivery", Int J Pharm, 2010, 392(1-2):224-31.

Zhang et al., "Helper lipid structure influences protein adsorption and delivery of lipid nanoparticles to spleen and liver", Biomater. Sci., 2021, 9:1449-1463.

Zhang et al., "Helper lipid structure influences protein adsorption and delivery of lipid nanoparticles to spleen and liver", Biomater. Sci, 2021, 9:1449-1463, Supplementary Information.

Albertsen et al., "The role of lipid components in lipid nanoparticles for vaccines and gene therapy", Advanced Drug Delivery Reviews, 2022, 188:114416.

International Searching Authority of the PCT, International Search Report and the Written Opinion of the International Searching Authority, Dec. 21, 2023, for PCT/CA2023/051416 having an international filing date of Oct. 25, 2023.

Jung et al., "Lipid nanoparticles for delivery of RNA therapeutics: Current status and the role of in vivo imaging", Theranostics, 2022, 12(17):7509-7531.

Niculescu et al., "New Applications of Lipid and Polymer-Based Nanoparticles for Nucleic Acids Delivery", Pharmaceutics, 2021, 13:2053.

Tenchov et al., "Lipid Nanoparticles—From Liposomes to mRNA Vaccine Delivery, a Landscape of Research Diversity and Advancement", ACS Nano, 2021, 15:16982-17015.

U.S. Appl. No. 63/195,269, dated Jun. 2021, Jayesh Kulkami.†

\* cited by examiner
† cited by third party

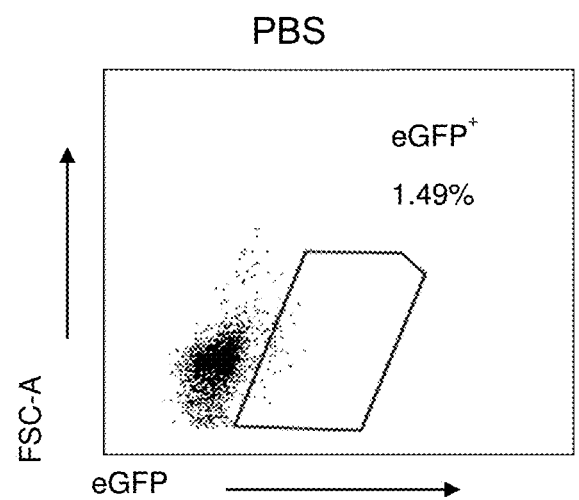
FIG 6A
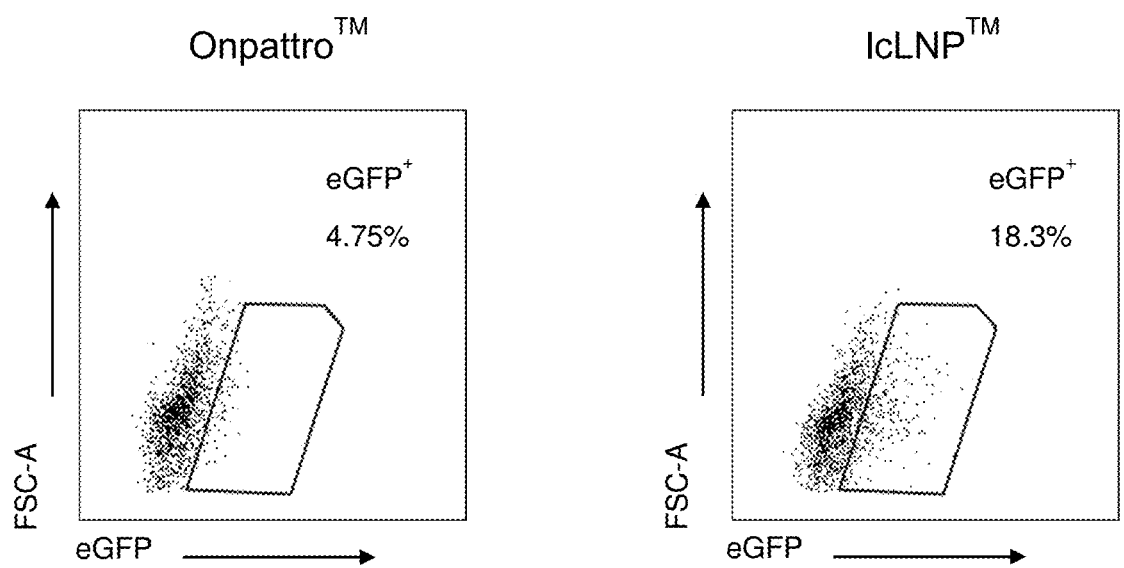
FIG 6B          FIG 6C

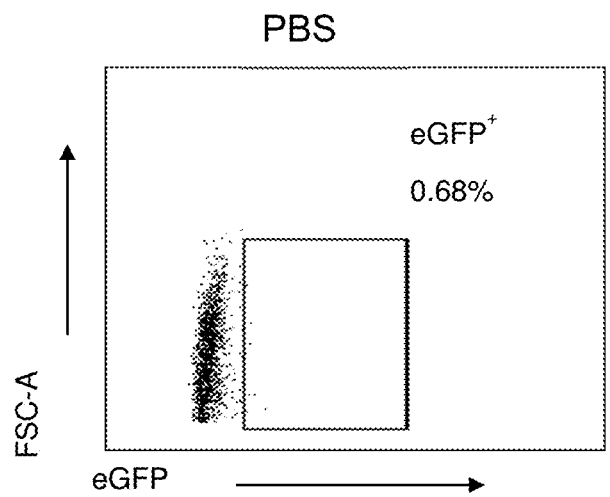
FIG. 8A
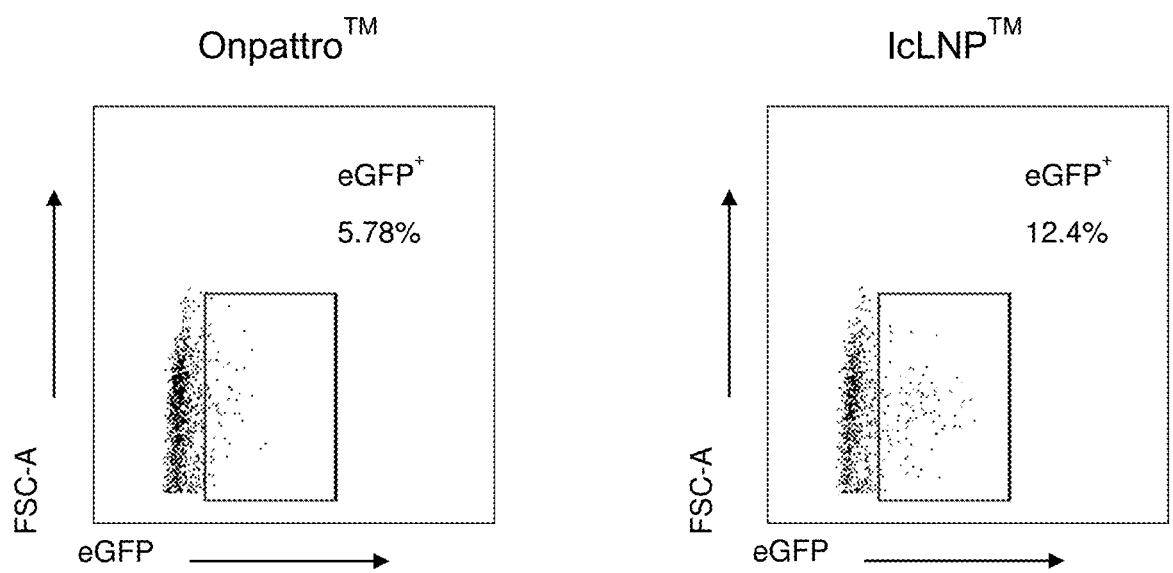
FIG. 8B                              FIG. 8C

MRNA DELIVERY COMPOSITION

INCORPORATION BY REFERENCE TO PRIORITY APPLICATION

This application claims priority to U.S. provisional Application Ser. No. 63/362,345, filed on Apr. 1, 2022, which is hereby expressly incorporated herein by reference in its entirety.

TECHNICAL FIELD

The present disclosure relates to methods of delivery of mRNA and compositions for delivery thereof to extrahepatic tissue.

BACKGROUND

Lipid nanoparticle (LNP) formulations represent a revolution in the field of nucleic acid delivery. An early example of a lipid nanoparticle product approved for clinical use is Onpattro™ Onpattro™ is a lipid nanoparticle-based short interfering RNA (siRNA) drug formulation for the treatment of polyneuropathies induced by hereditary transthyretin amyloidosis. The success of this LNP delivery system paved the way for the clinical development of the leading LNP-based COVID-19 mRNA vaccines.

The Onpattro™ LNP formulation consists of four main lipid components, namely: ionizable amino lipid, distearoylphosphatidylcholine (DSPC), cholesterol, and polyethylene glycol conjugated lipids (PEG-lipids) at respective molar amounts of 50/10/38.5/1.5. Onpattro™ is still considered the gold standard for comparison in studies of LNP-mediated efficacy and current approaches to LNP design make few deviations from the four-component system.

Of these four components, the ionizable lipid makes up the bulk of the Onpattro™ formulation (50 mol %) and is considered important for the in vitro and in vivo activity of the LNP. Accordingly, most work in the field has focused primarily on improving this lipid component. The ionizable lipid, which is typically an amino lipid, has been carefully designed so that it is charged at low pH and near-neutral at physiological pH. This allows for electrostatic interactions between the lipid and the negatively charged nucleic acid during initial formulation. Since the ionizable lipid is near neutral at physiological pH, toxicity and renal clearance is reduced. After cellular uptake by endocytosis, the acidic environment of the endosome leads to an increase in the net positive charge of the ionizable amino lipids, which promotes fusion with the anionic lipids of the endosomal membrane and subsequent membrane destabilization and release of the nucleic acid-based therapeutics into the cytoplasm to exert their effects.

With respect to the remaining three lipid components, the PEG-lipid is well known for improving circulation longevity of the LNP and cholesterol functions to stabilize the particle. Generally, however, comparatively less attention has been devoted to studying DSPC beyond its role as a structural lipid.

While strides have been made in research relating to LNP-mediated nucleic acid delivery, it is widely known that the Onpattro™ formulation largely accumulates in liver (hepatic) tissues. The ability of LNPs to accumulate in organs and tissues beyond the liver would greatly expand the clinical utility of these delivery systems. In order to improve the delivery of nucleic acid cargo to extrahepatic tissues, such as the bone marrow and spleen, the particles should exhibit enhanced circulation lifetimes. Traditional approaches to achieve this rely on optimizing the levels of PEG-lipid in the LNP, but the inclusion of PEG-lipids in LNPs often results in transfection potencies that are low or unfavorable immune responses.

Studies have been conducted in vivo to investigate the ability of four-component, Onpattro™-type formulations to deliver siRNA beyond the liver. In particular, siRNA gene silencing beyond the liver was investigated with Onpattro™-type LNPs (MC3/Chol/DSPC/PEG-DMG) incorporating DSPC at 10 and 40 mol % (Ordobadi, Lipid Nanoparticles for Delivery of Bioactive Molecules, 2019, A Thesis Submitted in Partial Fulfillment of the Requirements for the Degree of Doctor of Philosophy, The University of British Columbia). It was shown that the 10 mol % DSPC Onpattro™-like formulations had similar liver accumulation and blood circulation lifetimes as 40 mol % DSPC formulations (MC3/Chol/DSPC/PEG-DMG; 18.5/40/40/1.5 mol %). Further, the 40 mol % DSPC siRNA-LNP only performed comparably to 10 mol % DSPC formulations in bone marrow gene silencing. These previous studies thus showed no clear benefit resulting from adjusting the levels of DSPC to improve extrahepatic delivery of nucleic acid cargo.

The above studies investigating extrahepatic delivery were confined to LNPs having siRNA cargo. However, messenger RNA (mRNA) therapy is increasingly becoming an important tool to treat disease and the delivery of mRNA to extrahepatic tissues would expand the clinical utility of mRNA therapeutics beyond the liver. Similar to siRNA, the mRNA molecule rapidly degrades in the body, and so LNPs are used to reduce such degradation. Nonetheless, there are inherent chemical and structural differences between mRNA and siRNA in terms of length, stability and charge density of the nucleic acid. (Kauffman et al., 2015, NanoLetters, 15(11):7300-7306). Consequently, siRNA-LNP studies may not be informative for the design of LNPs for mRNA delivery. Further, present work on LNP mRNA systems for intravenous administration focusses primarily on developing improved ionizable cationic lipids. (Semple et al., Nat Biotechnol 2010, 28:172). In addition, these systems use the Onpattro™ lipid composition (see above) and have short circulation lifetimes with most of the cargo accumulating in the liver within 30 min. (Akinc et al., 2019, Nat Nanotechnol., 14:1084).

There is thus a need in the art to improve the in vivo extra hepatic delivery of nucleic acid, such as mRNA, using lipid nanoparticles.

SUMMARY

The present disclosure addresses one or more of the foregoing problems in the prior art and/or provides useful alternatives to known compositions for the delivery of mRNA.

The present disclosure is based on the finding that an ionizable LNP formulation (herein "lcLNP") that includes elevated levels of phosphatidylcholine lipid relative to an Onpattro™ benchmark LNP can significantly improve the in vivo extrahepatic delivery of mRNA. In some embodiments, the present disclosure provides an mRNA-LNP formulation that has improved in vivo expression of mRNA in extrahepatic tissues over an Onpattro™ LNP, as measured in a sub-set of immune cells in the bone marrow and spleen in an animal model at predetermined times after administration, such as at one hour and three hours post-administration.

In one aspect, the present disclosure provides a lipid nanoparticle for extrahepatic delivery of mRNA, the lipid nanoparticle comprising: (i) mRNA; (ii) a phosphatidylcholine lipid content of from 30 to 70 mol %; (iii) a ionizable content of from 5 mol % to 50 mol %; (iv) a sterol selected from cholesterol or a derivative thereof; and (v) a hydrophilic polymer-lipid conjugate that is present at a lipid content of 0.5 mol % to 5 mol %, wherein each lipid content is measured relative to a total lipid content of the lipid nanoparticle.

In another aspect, the present disclosure provides a lipid nanoparticle comprising encapsulated mRNA and 20 to 70 mol % of a phosphatidylcholine lipid relative to total lipid present in the lipid nanoparticle, an ionizable lipid; and at least one of a sterol and a hydrophilic polymer-lipid conjugate, the lipid nanoparticle exhibiting at least a 10% increase in gene expression of the mRNA in vivo as measured in a sub-set of cells from the bone marrow or spleen selected from macrophages, monocytes and/or T-cells at 24 hours and/or 3 days post-injection as compared to an Onpattro-type formulation of MC3/DSPC/cholesterol/PEG-lipid at 50/10/38.5/1.5, mol:mol encapsulating the mRNA, but otherwise measured under identical conditions, wherein the gene expression is quantified in an animal model by detection of cells positive for green fluorescent protein (GFP) using flow cytometry.

In one embodiment, the phosphatidylcholine lipid is distearoylphosphatidylcholine (DSPC), dioleoylphosphatidylcholine (DOPC), 1-palmitoyl-2-oleoyl-phosphatidylcholine (POPC) or dipalmitoyl-phosphatidylcholine (DPPC).

In another embodiment, the phosphatidylcholine lipid is distearoylphosphatidylcholine (DSPC).

In a further embodiment, the phosphatidylcholine content is between 40 mol % and 60 mol %. In another embodiment, the phosphatidylcholine content is between 42 mol % and 58 mol %. In yet a further embodiment, the phosphatidylcholine content is between 45 mol % and 55 mol %.

In another embodiment, the ionizable lipid is a cationic lipid. In a further embodiment, the ionizable cationic lipid is an amino lipid.

In a further embodiment, the ionizable lipid is present at less than 40 mol %.

In a further embodiment, the hydrophilic polymer-lipid conjugate is a polyethyleneglycol-lipid conjugate. In a further embodiment, the sterol is present at from 15 mol % to 45 mol % based on the total lipid present in the lipid nanoparticle. In another embodiment, the sterol is present at from 18 mol % to 40 mol % based on the total lipid present in the lipid nanoparticle.

In a further embodiment, the lipid nanoparticle exhibits at least a 10% increase in gene expression of the mRNA in vivo as measured in a sub-set of cells from the bone marrow or spleen selected from macrophages, monocytes and/or T-cells at 24 hours and/or 3 days post-injection as compared to an Onpattro-type formulation of MC3/DSPC/cholesterol/PEG-lipid at 50/10/38.5/1.5, mol:mol encapsulating the mRNA, but otherwise measured under identical conditions, wherein the gene expression is quantified in an animal model by detection of cells positive for green fluorescent protein (GFP) using flow cytometry. In a further embodiment, the green fluorescent protein is measured in a macrophage/monocyte cell population isolated from the spleen or liver of the mouse post-injection and wherein the increase in expression is determined by measuring a percentage of cells in the cell population that are positive for the eGFP.

In another embodiment, the green fluorescent protein is measured 3 days post-injection and wherein the animal model is a mouse.

In a further embodiment, the in vivo expression of green fluorescent protein in a macrophage/monocyte cell population isolated from the bone marrow or spleen of the mouse post injection is increased by at least 50% over a sphingomyelin-containing LNP that substitutes sphingomyelin for the DSPC but otherwise has an identical lipid composition as the lipid nanoparticle.

In another aspect, there is provided a method for in vivo delivery of mRNA to a mammalian subject, the method comprising: administering to the mammalian subject a lipid nanoparticle as described in any embodiment or aspect above.

In further embodiments, the mRNA accumulates in the spleen or bone marrow of the subject at least one day post-administration.

In another embodiment, the disease or disorder is an autoimmune disorder. In a further embodiment, the disease or disorder is an infectious disease. In a further embodiment, the disease or disorder is cancer.

In further embodiment, there is provided use of the lipid nanoparticle for in vivo or in vitro delivery and expression of the mRNA to mammalian cells.

In another embodiment, there is provided use of the lipid nanoparticle as described above for the manufacture of a medicament for in vivo or in vitro delivery of the mRNA to mammalian cells. In some embodiments, the mRNA is used to target an autoimmune disorder in vivo. In further embodiments, the mRNA is used to target an infectious disease in vivo.

In a further embodiment, the mRNA is used to target a cancer in vivo.

BRIEF DESCRIPTION OF THE DRAWINGS

FIG. 6A shows a representative scatter plot depicting the percentage of eGFP T cells in the bone marrow at 24 hours post-injection of phosphate buffered saline to mice.

FIG. 6B shows a representative scatter plots depicting the percentage of eGFP T cells in the bone marrow at 24 hours post-injection of eGFP-mRNA LNPs having 10 mol % DSPC (MC3:DSPC:Chol:PEG-lipid (50:10:38.5:1.5) ("Onpattro™") to mice.

FIG. 6C shows a representative scatter plot depicting the percentage of eGFP T cells in the bone marrow at 24 hours post-injection of eGFP-mRNA LNPs having 50 mol % DSPC (MC3:DSPC:Chol:PEG-lipid (27.4:50:21.1:1.5 mol: mol) ("1cLNP™") to mice.

FIG. 8A shows a representative scatter plot depicting the percentage of eGFP monocytes/macrophages in the spleen at 24 hours post-injection of phosphate buffered saline (PBS) to mice.

FIG. 8B shows a representative scatter plot depicting the percentage of eGFP monocytes/macrophages in the spleen at 24 hours post-injection of eGFP-mRNA LNPs having 10 mol % DSPC (MC3:DSPC:Chol:PEG-lipid (50:10:38.5:1.5) ("Onpattro™")) to mice.

FIG. 8C shows a representative scatter plot depicting the percentage of eGFP monocytes/macrophages in the spleen at 24 hours post-injection of eGFP-mRNA LNPs having 50 mol % DSPC (MC3:DSPC:Chol:PEG-lipid (27.4:50:21.1: 1.5 mol:mol) ("1cLNP™") to mice.

FIG. 10B)) to mice.

DETAILED DESCRIPTION

Figure 1A:
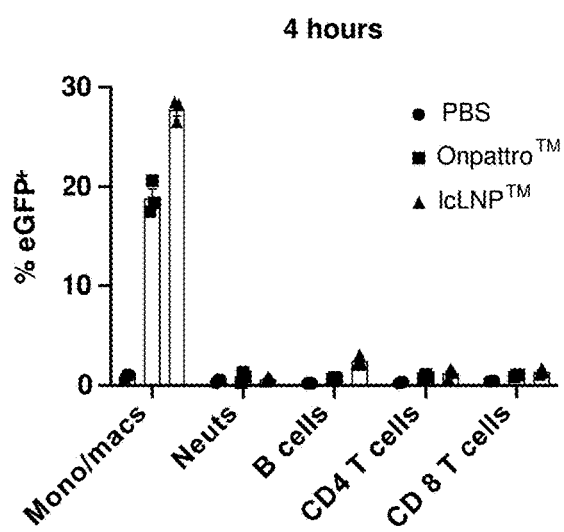
FIG. 1A show the percentage of enhanced green fluorescent protein (eGFP) positive cells (% eGFP) in the spleen of immune cell sub-populations as indicated (monocytes/macrophages, neutrophils, B cells, CD4 T cells and CD8 T cells) after 4 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice. MF019 and nMC3 are ionizable cationic lipids as described herein (Example 1).

The lipid nanoparticle described herein is an improvement over the conventional four-component LNP used for delivery of siRNA, referred to herein as Onpattro™. In certain advantageous embodiments, the LNP is an improved formulation that comprises ionizable lipid, a phosphatidylcholine lipid; cholesterol and a hydrophilic polymer-lipid conjugate, and in which the phosphatidylcholine lipid is present at a mol % of at least 20 mol % or at least 30 mol % and in which the ionizable lipid is present at less than 40 mol %. At set forth herein, elevated phosphatidylcholine mol % beyond what is used in conventional formulations for nucleic acid delivery provides surprising increases in mRNA delivery to extrahepatic tissues relative to the benchmark Onpattro™ formulation.

The lipid nanoparticle described herein comprises a cargo that is messenger RNA. As used herein, the term "messenger RNA" or "mRNA", refers to a polynucleotide that encodes and expresses at least one peptide, polypeptide or protein. The term is meant to include, but is not limited to, small activating RNA (saRNA) and trans-amplifying RNA (taRNA).

As used herein, the term "encapsulation," with reference to incorporating the mRNA within a lipid nanoparticle refers to any association of the mRNA with any lipid component or compartment of the lipid nanoparticle. In one example of the disclosure, the mRNA is present in the core of the LNP.

The concentration of mRNA in the LNP may be between 0.01 and 20 mg/mL or between and 10 mg/mL or between 0.05 and 5 mg/mL or between 0.075 and 4 mg/mL.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is chemically synthesized, the mRNA can comprise nucleoside analogs such as analogs having chemically modified bases or sugars, and/or backbone modifications. In some embodiments, an mRNA is or comprises natural nucleo sides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNAs of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to formulate mRNAs of a variety of lengths. In some embodiments, the present disclosure may be used to formulate and encapsulate in vitro synthesized mRNA ranging from about about 250 bp to 20 kb, about 500 bp –20 kb, about 1-15 kb, about 1-10 kb, about 5-20 kb, about 5-15 kb, about 5-12 kb, about 5-10 kb, about 8-20 kb, or about 8-15 kb in length.

Typically, mRNA synthesis includes the addition of a "cap" on the 5' end, and a "tail" on the 3' end. The presence of the cap provides resistance to nucleases found in most eukaryotic cells. The presence of a "tail" serves to protect the mRNA from exonuclease degradation.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between and 500 nucleotides in length or longer.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences are incorporated into mRNA for in vivo studies in animal models to assess biodistribution.

Phosphatidylcholine Lipid

The LNP generally includes one or more structural lipids, meaning an amphipathic lipid that allows for the formation of particles and generally bears no net charge at physiological pH. The term includes zwitterionic lipids that have substantially no charge at physiological pH, and includes phospholipids.

In some embodiments, the structural lipid is a phosphatidylcholine lipid selected from distearoylphosphatidylcholine (DSPC), dioleoylphosphatidylcholine (DOPC), 1-palmitoyl-2-oleoyl-phosphatidylcholine (POPC) and dipalmitoyl-phosphatidylcholine (DPPC). The structural lipid content may include mixtures of two or more types of different structural lipids. In one embodiment, the phosphatidylcholine lipid content is a mixture of DSPC and DOPC and POPC. In such embodiments, the mixture may have a DSPC content of at least 20 or 30 mol %.

The structural lipid content in some embodiments is greater than 20 mol %, greater than mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of helper lipid content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the phosphatidylcholine lipid content is from 20 mol % to 80 mol % or 25 mol % to 60 mol % or 30 mol % to 60 mol % or 35 mol % to 60 mol % or 40 mol % to 60 mol % or 42 mol % to 58 mol %, or 43 mol % to 57 mol % or 44 mol % to 56 mol % or mol % to 55 mol % of total lipid present in the lipid nanoparticle.

In one embodiment, the structural lipid is DSPC. For example, in certain embodiments, the DSPC lipid content is from 20 mol % to 80 mol % or 25 mol % to 60 mol % or 30 mol % to 60 mol % or 35 mol % to 60 mol % or 40 mol % to 60 mol % or 42 mol % to 58 mol %, or 43 mol % to 57 mol % or 44 mol % to 56 mol % or 45 mol % to 55 mol % of total lipid present in the lipid nanoparticle.

In some embodiments, the inclusion of sphingomyelin is undesirable (e.g., see Example 2). The sphingomyelin content of the lipid nanoparticle in some embodiments is less than 5 mol %, less than 4 mol %, less than 3 mol %, less than 2 mol %, less than 1 mol %, less than 0.75 mol %, or less than 0.5 mol %. In some embodiments, the LNP is "sphingomyelin-free", meaning there is no sphingomyelin in the LNP or substantially sphingomyelin-free, meaning there is less than 5 mol % sphingomyelin.

The LNP may comprise additional structural lipids besides a phosphatidylcholine lipid. For example, the LNP may comprise structural lipids that have a net positive or negative charge at physiological pH. Generally, such lipids will be present at less than 10 mol % or less than 5 mol %.

The structural lipid content is determined based on the total amount of lipid in the lipid nanoparticle, including the sterol.

Ionizable Lipid

The LNP of the disclosure has an ionizable lipid. The ionizable lipid may be charged at low pH and have substantially no net charge at physiological pH. This allows for electrostatic interactions between the lipid and the negatively charged nucleic acid cargo during initial formulation. Since the ionizable lipid is near neutral at physiological pH, toxicity and renal clearance is reduced. After cellular uptake by endocytosis, the acidic environment of the endosome leads to an increase in the net positive charge of the ionizable amino lipids, which promotes fusion with the anionic lipids of the endosomal membrane and subsequent membrane destabilization and release of the nucleic acid-based therapeutics into the cytoplasm to exert their effects.

In some embodiments, it is desirable to include less than 50 mol % ionizable lipid. That is, the ionizable lipid content may be less than 50 mol %, less than 45 mol %, less than 40 mol %, less than 35 mol %, less than 30 mol %, less than 25 mol %, less than 20 mol %, less than 15 mol %, less than 10 mol % or less than 5 mol %.

In certain embodiments, the ionizable lipid content is from 5 mol % to 50 mol % or 8 mol % to 47 mol % or 10 mol % to 50 mol % or 15 mol % to 45 mol % or 15 mol % to 35 mol % of total lipid present in the lipid nanoparticle.

As used herein, the term "cationic lipid" refers to a lipid that, at a given pH, such as physiological pH, is in an electrostatically neutral form and that may either accept or donate protons, thereby becoming electrostatically positively charged, and for which the electrostatically neutral form has a calculated logarithm of the partition coefficient between water and 1-octanol (i.e., a cLogP) greater than 8. In some embodiments, the cationic lipid has a pKa that is between and 8.0.

In some embodiments, the cationic lipid has an amino group. In some embodiments, the cationic lipid comprises a protonatable tertiary amine (e.g., pH titratable) head group, C16 to C18 alkyl chains, ether linkages between its head group and alkyl chains, and 0 to 3 double bonds. Such lipids include, but are not limited to sulfur lipids, such as MF019 described herein and DODMA. Other lipids that may be used in the practice of the disclosure include MC3—and KC2-type lipids, which are well-known to those of skill in the art. In further embodiments, the ionizable lipid is selected from one or more lipids set forth in WO 2022/246555; WO 2022/246568; WO 2022/24657; WO2022/155728; PCT/CA2023/050129 filed on Jan. 31, 2023; U.S. provisional application No. 63/340,687 filed on May 11, 2022; U.S. provisional application No. 63/410,281 filed on Sep. 27, 2022; U.S. provisional application No. 63/410,261 filed on Sep. 27, 2022; U.S. provisional application No. 63/434,506 filed on Dec. 22, 2022; U.S. provisional application No. 63/410,273 filed on Sep. 27, 2022; and U.S. provisional application No. 63/445,854 filed on Feb. 15, 2023, each incorporated herein by reference.

In one embodiment, the ionizable cationic lipid comprises an ionizable amino head group and at least two lipophilic groups, at least one of which comprises a heteroatom, such as an ester or one or more sulfur atoms. In some embodiments, at least one lipophilic group comprises distal branching and/or one or more cyclic groups. Examples of ionizable cationic lipids comprising an ionizable amino head group and two lipophilic chains, at least one chain comprising one or more sulfur atoms and/or ester groups are described in co-owned and co-pending U.S. provisional application No. 63/340,687 filed on May 11, 2022; U.S. provisional application No. 63/410,281 filed on Sep. 27, 2022; U.S. provisional application No. 63/410,261 filed on Sep. 27, 2022; U.S. provisional application No. 63/434,506 filed on Dec. 22, 2022; and U.S. provisional application No. 63/410,273 filed on Sep. 27, 2022, each incorporated herein by reference. Functional groups comprising one or more heteroatoms may be biodegradable in vivo.

In one embodiment, the ionizable cationic lipid has a protonatable amino head group; at least two lipophilic moieties, wherein the amino head group has a central nitrogen atom or carbon atom to which each of the two lipophilic moieties are directly bonded; each lipophilic chain has between 15 and 40 carbon atoms in total; and wherein the lipid has (i) a pK a of between 6 and 7.5; and (ii) a log P of at least 11.

Optionally, at least one of the lipophilic moieties bonded to the head group has a biodegradable group. In one non-limiting example, at least one of the lipophilic moieties has the formula:

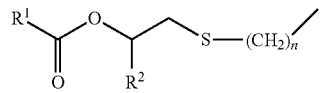

In one embodiment, $R^1$ and $R^2$ are, independently, linear, cyclic or branched optionally substituted $C_3$-$C_{20}$ alkyl and optionally with varying degrees of unsaturation; and n is 4 to 8.

In some embodiments, it is desirable to include less than 50 mol % ionizable cationic lipid in the LNP. That is, the ionizable cationic lipid content may be less than 50 mol %, less than 45 mol %, less than 40 mol %, less than 35 mol %, less than 30 mol %, less than 25 mol %, less than 20 mol %, less than 15 mol %, less than 10 mol % or less than 5 mol %.

In certain embodiments, the ionizable cationic lipid content is from 5 mol % to 50 mol % or 8 mol % to 47 mol % or 10 mol % to 50 mol % or 15 mol % to 45 mol % or 15 mol % to 35 mol % of total lipid present in the lipid nanoparticle.

The ionizable lipid component may include an ionizable anionic lipid as part of the ionizable lipid content. An example of such a lipid is cholesteryl hemisuccinate (CHEMS). Further examples of ionizable anionic lipids are described in co-pending and co-owned U.S. provisional patent application No. 63/453,766 titled "Ionizable Anionic Lipids" filed on Mar. 22, 2023, which is incorporated herein by reference in its entirety.

Sterol

The LNP further includes a sterol in some embodiments. The term "sterol" refers to a naturally-occurring or synthetic compound having a gonane skeleton and that has a hydroxyl moiety attached to one of its rings, typically the A-ring.

Examples of sterols include cholesterol, or a cholesterol derivative, the latter referring to a cholesterol molecule having a gonane structure and one or more additional functional groups.

The cholesterol derivative includes f3-sitosterol, 3-sitosterol, campesterol, stigmasterol, fucosterol, or stigmastanol, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β[N-(N'N'-dimethylaminoethyl)carbamoyl cholesterol (DC-Chol), 24(S)-hydroxychole sterol, 25-hydroxychole sterol, 25(R)-27-hydroxychole sterol, 22-oxachole sterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-chole steryl-3e-ol, dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol or a salt or ester thereof.

In one embodiment, the sterol is present at from 15 mol % to 50 mol %, 18 mol % to 45 mol %, 20 mol % to 45 mol %, 25 mol % to 45 mol % or 30 mol % to 45 mol % based on the total lipid present in the lipid nanoparticle.

In another embodiment, the sterol is cholesterol and is present at from 15 mol % to 50 mol %, 18 mol % to 45 mol %, 20 mol % to 45 mol %, 25 mol % to 45 mol % or 30 mol % to 45 mol % based on the total lipid present in the lipid nanoparticle.

In another embodiment, the sterol is a cholesterol derivative and is present at from 15 mol % to 50 mol %, 18 mol % to 45 mol %, 20 mol % to 45 mol %, 25 mol % to 45 mol % or 30 mol % to 45 mol % based on the total lipid present in the lipid nanoparticle.

In one embodiment, the combined (i) sterol content (e.g., cholesterol or cholesterol derivative thereof); and (ii) neutral lipid content is at least 50 mol %; at least 55 mol %, at least 60 mol %, at least 65 mol %, at least 70 mol %, at least 75 mol %, at least 80 mol % or at least 85 mol % based on the total lipid present in the lipid nanoparticle.

Hydrophilic Polymer-Lipid Conjugate

In one embodiment, the lipid nanoparticle comprises a hydrophilic-polymer lipid conjugate capable of incorporation into the LNP. The conjugate includes a vesicle-forming lipid having a polar head group, and covalently attached to the head group, a polymer chain that is hydrophilic. Examples of hydrophilic polymers include polyethyleneglycol (PEG), polyvinylpyrrolidone, polyvinylmethylether, polyhydroxypropyl methacrylate, polyhydroxypropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate. The hydrophilic polymer lipid conjugate may also be a naturally-occurring or synthesized oligosaccharide-containing molecule, such as monosialoganglioside ($G_{M1}$). The ability of a given hydrophilic-polymer lipid conjugate to enhance the circulation longevity of the LNPs herein could be readily determined by those of skill in the art using known methodologies.

The hydrophilic polymer lipid conjugate may be present in the nanoparticle at 0.5 mol % to 5 mol %, or at 0.5 mol % to 3 mol %, or at 0.5 mol % to 2.5 mol % or at 0.5 mol % to 2.0 mol % or at 0.5 mol % to 1.8 mol % of total lipid. In certain embodiments, the hydrophilic polymer lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

In another embodiment, the PEG-lipid conjugate is present in the nanoparticle at 0.5 mol % to 5 mol %, or at 0.5 mol % to 3 mol % or at 0.5 mol % to 2.5 mol % or at 0.5 mol % to 2.0 mol % or at 0.5 mol % to 1.8 mol % of total lipid. In certain embodiments, the PEG-lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

Nanoparticle Preparation and Morphology

Delivery vehicles incorporating the mRNA can be prepared using a variety of suitable methods, such as a rapid mixing/ethanol dilution process. Examples of preparation methods are described in Jeffs, L. B., et al., Pharm Res, 2005, 22(3):362-72; and Leung, A. K., et al., The Journal of Physical Chemistry. C, Nanomaterials and Interfaces, 2012, 116(34): 18440-18450, each of which is incorporated herein by reference in its entirety.

Without being bound by theory, the mechanism whereby a lipid nanoparticle comprising encapsulated mRNA can be formed using the rapid mixing/ethanol dilution process can be hypothesized as beginning with formation of a dense region of hydrophobic mRNA-ionizable lipid core at low pH (e.g., pH 4) surrounded by a monolayer of helper lipid/cholesterol that fuses with smaller empty vesicles as the pH is raised due to the conversion of the ionizable cationic lipid to the neutral form. As the proportion of bilayer helper lipid increases, the bilayer lipid progressively forms blebs and the ionizable lipid migrates to the interior hydrophobic core. At high enough helper lipid contents, the exterior bilayer preferring helper lipid can form a complete lipid layer, such as a continuous or discontinuous bilayer, around the interior trapped volume.

The LNP may comprise a "core" region. Surprisingly, it has been observed that the core is non-homogeneous in that it includes both an electron dense region and an aqueous portion or compartment as visualized by cryo-EM microscopy. In some embodiment, the core may be characterized as non-solid. Without being limiting, the electron dense region within the core may be partially surrounded by the aqueous portion or compartment within the enclosed space as observed by cryo-TEM. The aqueous portion may form a distinct aqueous region or compartment within the lipid nanoparticle. In other words, it is believed that the aqueous portion or compartment is not merely a hydration layer. Such non-solid core particles are described in co-owned and co-pending WO 2022/251959, the contents of which are incorporated herein by reference.

In one embodiment, at least one about fifth of the core (trapped volume) contains the aqueous portion or compartment, and in which the electron dense region within the core is partially contiguous with the lipid layer comprising the bilayer, as determined qualitatively by cryo-EM. In another embodiment, at least one about quarter of the core contains the aqueous portion or compartment, and in which the electron dense core is either partially contiguous with the lipid layer comprising the bilayer, as determined qualitatively by cryo-EM. In a further embodiment, at least one about one third of the core contains the aqueous portion or compartment, and in which the electron dense region is either partially contiguous with the lipid layer comprising the bilayer, as determined qualitatively by cryo-EM. In another embodiment, at least one about one half of the core contains the aqueous portion or compartment, and in which the electron dense core is either partially contiguous with the lipid layer comprising the bilayer, as determined qualitatively by cryo-EM.

In another embodiment, the electron dense region of the LNP surprisingly appears to be completely surrounded by the aqueous portion of the core as visualized by cryo-TEM microscopy. This morphology is observed in a single plane and a portion of the electron dense region as observed is contiguous with the lipid layer (e.g., bilayer) but cannot be seen since this portion is not within the plane that can be visualized.

In one embodiment, the electron dense region is generally spherical in shape. In another embodiment, the electron dense region is hydrophobic.

The lipid nanoparticles herein may exhibit particularly high trapping efficiencies of mRNA. Thus, in one embodiment, the trapping efficiency is at least 50, 55, 60, 65, 70, 75, 80, 85 or 90%.

In one embodiment, the mRNA is at least partially encapsulated in the electron dense region. For example, in one embodiment, at least 50, 60, 70 or 80 mol % of the mRNA is encapsulated in the electron dense region. In another embodiment, at least 50, 60, 70 or 80 mol % of the ionizable lipid is in the electron dense region.

In another embodiment, the mRNA and cationic lipid are present in the electron dense region. In a further embodiment, the helper lipid is present in the lipid layer comprising the bilayer.

The lipid nanoparticle may comprise a single bilayer or may be a combination of a bilayer and a monolayer in some embodiments. In one embodiment, the lipid layer is a continuous bilayer that surrounds the core.

In certain embodiments the electron dense region of the core is separated from the lipid layer comprising the bilayer by the aqueous portion or compartment. For example, the disclosure provides a lipid nanoparticle preparation comprising a plurality of lipid nanoparticles in which at least 20%, 30%, 40%, 50%, 60% or 70% of the particles as determined by cryo-EM microscopy have a core with an electron dense region and an aqueous portion or compartment and in which the aqueous portion or compartment is partially surrounded by the lipid layer comprising the bilayer as visualized by cryo-EM microscopy.

In another embodiment, and without being limiting, the disclosure provides a lipid nanoparticle preparation comprising a plurality of lipid nanoparticles in which generally at least 10%, 20%, 30%, 40%, 50%, 60% or 70% of the particles have an elongate shape (e.g., generally oval-shaped) as determined qualitatively by cryo-EM microscopy. In this latter embodiment, the electron dense region of the core may be partially surrounded the aqueous space as visualized by cryo-EM microscopy.

In one embodiment, the lipid nanoparticle is part of a preparation of lipid nanoparticles, and wherein the electron dense region of at least 20% of the lipid nanoparticles are either (i) enveloped by the aqueous portion, or (ii) is partially surrounded by the aqueous portion and wherein a portion of a periphery of the electron dense region is contiguous with the lipid layer, as visualized by cryo-EM microscopy in a single plane.

In certain embodiments, the disclosure provides a lipid nanoparticle preparation comprising a plurality of lipid nanoparticles in which generally at least 10%, 20%, 30%, 40%, 50%, 60% or 70% of the particles as determined by cryo-EM microscopy have a core with an electron dense region that is contiguous with the lipid layer comprising the bilayer as visualized by cryo-EM microscopy.

In another embodiment, and without being limiting, the disclosure provides a lipid nanoparticle preparation comprising a plurality of lipid nanoparticles in which generally at least 10%, 20%, 30%, 40%, 50%, 60% or 70% of the particles have a core comprising an electron dense region that appears to be surrounded or enveloped by a continuous aqueous space disposed between the lipid layer (e.g., bilayer) and the electron dense region, as visualized in one plane by cryo-EM microscopy.

LNPs are visualized by cryo-TEM as described in the Example section hereinafter.

In another embodiment, the polydispersity index (PDI) of the LNP preparation is less than 0.15, 0.12 or 0.10.

In another embodiment, the particle size distribution is such that at least 90% of the particles in the LNP preparation of the disclosure have a diameter of between 40 nm and 200 nm, between 45 and 150 nm or between 50 and 140 nm.

The lipid nanoparticles herein may exhibit particularly high encapsulation efficiencies of nucleic acid. As used herein, the term "encapsulation," with reference to incorporating the nucleic acid within a lipid nanoparticle refers to any association of the nucleic acid with any lipid component or compartment of the lipid nanoparticle, including a lipophilic or the aqueous portion. In one embodiment, the nucleic acid is present at least in the core of the LNP.

In one embodiment, the encapsulation efficiency is at least 50, 55, 60, 65, 70, 75, 80, 85, 90% or 92%. The encapsulation efficiency of the nucleic acid is determined as set forth in the Materials and Methods section in the Examples herein.

Embodiments of the present disclosure also provide lipid nanoparticles described according to the molar ratio between the positively charged amine groups of the amine lipid (N) and the negatively charged phosphate groups (P) of the oligonucleotide to be encapsulated. This may be mathematically represented by the equation N/P. In one embodiment, the N/P ratio of the lipid nanoparticle is between 4 and 15 or between 4.5 and 10 or between 5 and 10 or between 5.5 and 8.

In one embodiment, the N/P ratio of the lipid nanoparticle is at least 4, 4.25, 4.50, 4.75, 5.25, 5.5, 5.75, 6.0 or 6.25. The upper limit may be 15, 14, 13, 12, 11, 10, 9 or 8. The disclosure also encompasses a combination of any two of the upper and lower limits.

In one embodiment, the lipid nanoparticle has a weight nucleic acid/micromole of total lipid that is 0.05:1 to 1:1. In one embodiment, the lower limit is 0.06:1, 0.08:1, 0.10:1, 0.12:1, 0.16:1, 0.18:1, 0.20:1, 0.22:1, 0.24:1, 0.26:1, 0.28:1, 0.30:1, 0.32:1, 0.34:1, 0.36:1, 0.38:1 or 0.40:1 weight nucleic acid/micromole of total lipid. In another embodiment, the upper limit is 0.82:1, 0.84:1, 0.86:1, 0.88:1, 0.90:1, 0.92:1, 0.94:1, 0.96:1 or 0.98:1 weight nucleic acid/micromole of total lipid. The disclosure also encompasses a combination of any two of the upper and lower limits.

In one embodiment, the mRNA copy number/LNP is 1-10 or 4-8.

Improved Gene Expression in Spleen and/or Bone Marrow

As used herein, "expression" of an mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme).

As described in Example 1, the LNPs of the disclosure may provide improved mRNA delivery to a wider range of tissues than previous Onpattro™ formulations for mRNA delivery, including but not limited to delivery to the spleen and/or bone marrow. Whether or not a lipid particle exhibits such enhanced delivery to a given tissue or organ can be determined by biodistribution studies in an in vivo mouse model. In such embodiments, enhanced green fluorescent protein (eGFP) may be used to detect mRNA expression in a given tissue or organ. In particular, according to such embodiments, LNP mRNA systems are prepared encapsulating mRNA coding for eGFP and biodistribution and GFP expression in cell populations in the spleen and bone marrow are evaluated using flow cytometry following systemic administration.

To assess whether a given lipid nanoparticle exhibits an increase in gene expression in a relevant tissue or organ at 12 hours, 24 hours, 48 hours or 3 days post-injection, the mRNA-LNP of the disclosure is compared to the Onpattro™-type formulation of Example 1. The two LNPs being compared are subjected to the same experimental methods and materials to determine in vivo expression as set forth in Example 1.

In one embodiment, the lipid nanoparticle exhibits at least a 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290% or 300% increase in gene expression of an encapsulated mRNA encoding enhanced GFP (eGFP) as measured in vivo in spleen and/or bone marrow immune cell population sub-sets at 24 hours and/or 3 days post-injection as compared to a lipid nanoparticle encapsulating eGFP-mRNA with an Onpattro™-type formulation of nor-MC3/DSPC/cholesterol/PEG-lipid at 50/10/38.5/1.5; mol:mol, wherein the gene expression is measured in a mouse model by detection of the eGFP translated from the mRNA. The measurement is carried out using flow cytometry and gene expression as determined by quantifying % positive cell counts in a given immune cell subset as set forth in Example 1. The percentage increase is determined by comparing the percentage positive cells (i.e., detection of eGFP) in a given cell type in the spleen or bone marrow and comparing this percentage to the percentage of positive cells resulting from injecting the Onpattro™ formulation using otherwise identical materials and methods.

In one embodiment, the immune cell sub-sets selected are from the spleen and are selected from one or more of monocytes/macrophages, neutrophils, B cells, CD4 T cells and/or CD8 T cells. In one embodiment, the immune cell sub-sets quantified for eGFP expression are from the spleen and are monocytes/macrophages (either or both cell types) and the increased expression is measured by determining positive cell counts (% positive for eGFP) by flow cytometry at 24 hours or 3 days post-injection. In another embodiment, the immune cell sub-sets in the spleen are monocytes/macrophages and positive cell counts (% positive for eGFP) are determined at 3 days post-injection.

In one embodiment, the immune cell sub-sets selected are from the bone marrow and are selected from one or more of erythroid, B cells, T-cells, monocytes/macrophages and neutrophils. In one embodiment, the immune cell sub-sets quantified for expression are from the bone marrow and are monocytes/macrophages or T-cells and the increased expression is measured by determining positive cell counts (% positive for eGFP) by flow cytometry at 24 hours or 3 days post-injection. In another embodiment, the immune cell sub-sets in the spleen are monocytes/macrophages or T-cells and positive cell counts (% positive for eGFP) are determined at 3 days post-injection.

Clinical and Non-Clinical Uses of the LNP Herein

In some embodiments, the lipid nanoparticle comprising mRNA is part of a pharmaceutical composition and is administered to treat and/or prevent a disease condition. The treatment may provide a prophylactic (preventive), ameliorative or a therapeutic benefit. The pharmaceutical composition will be administered at any suitable dosage.

The LNPs described herein may be used to treat and/or prevent any disease, disorder or condition in a mammalian subject. This includes a disease, disorder or condition, such as cancer, infectious diseases such as bacterial, viral, fungal or parasitic infections, inflammatory and/or autoimmune disorders, including treatments that induce immune tolerance and cardiovascular diseases such as hypertension, cardiac arrhythmia and restenosis.

Examples of cancers include lung cancer, colon cancer, rectal cancer, anal cancer, bile duct cancer, small intestine cancer, stomach (gastric) cancer, esophageal cancer; gallbladder cancer, liver cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma.

Non-limiting examples of other diseases, disorders or conditions that may be treated by the mRNA-LNPs herein and that may be attributed at least in part to an immunological disorder include colitis, Crohn's disease, allergic encephalitis, allograft transplant/graft vs. host disease (GVHD), diabetes and multiple sclerosis.

The LNPs herein may also be used in other applications besides the treatment and/or prevention of a disease or disorder. The LNPs may be used to treat conditions such as aging, preventative medicine and/or as part of a personalized medicine regime. In further embodiments, the LNP is used in a diagnostic application.

In one embodiment, the LNP is part of a pharmaceutical composition administered parenterally, i.e., intra-arterially, intravenously, subcutaneously or intramuscularly. In yet a further embodiment, the pharmaceutical compositions are for intra-tumoral administration. In another embodiment, the pharmaceutical compositions are administered intranasally, intravitreally, subretinally, intrathecally or via other local routes.

The pharmaceutical composition comprises pharmaceutically acceptable salts and/or excipients.

The compositions described herein may be administered to a patient. The term patient as used herein includes a human or a non-human subject.

The examples below are intended to illustrate the preparation of specific lipid nanoparticle mRNA preparations and properties thereof but are in no way intended to limit the scope of the invention.

EXAMPLES

Materials and Methods
LNP Preparation

The LNPs were prepared by dissolving mRNA in 25 mM sodium acetate, pH 4.0, while the lipid components at the mole % specified were dissolved in absolute ethanol. The lipids in ethanol and the eGFP mRNA in buffer were combined in a 1:3 volume by volume ratio using a t-junction with dual-syringe. The solutions were pushed through the t-junction at a combined flow rate of 20 mL/min (5 mL/minute for the lipid-containing syringe, 15 mL/minute for the mRNA-containing syringe). The mixture was subsequently dialyzed overnight against ~100 volumes of 1× phosphate buffered saline, pH 7.4 using Spectro/Por dialysis membranes (molecular weight cut-off 12 000-14 000 Da). The LNPs were concentrated as required with an Amicon Ultra™ 10 000 MWCO (molecular weight cut-off), regenerated cellulose concentrator.

Encapsulation efficiency was calculated by determining unencapsulated mRNA content by measuring the fluorescence upon the addition of RiboCireen™ to the mRNA-LNP ($F_i$) and comparing this value to the total mRNA content that is obtained upon lysis of the LNP by 2% Triton X-100 ($F_t$): % encapsulation=$(F_t-F_i)/F_t \times 100$.

The particle size and polydispersity index (PDI) were characterized using a Zetasizer Nano ZS™.

Flow Cytometry In Vivo Studies

The LNPs at the eGFP mRNA concentration of 0.1 mg/mL were injected intravenously (i.v.) in mice at a volume using the formula weight of the mouse (in grams)*10 Spleen and bone marrow were harvested at 4 hours, 1 day and 3 days after the LNP injections.

The spleen and bone marrow were harvested and processed into a single cell suspension. In particular, the mice were anesthetized with 5% isoflurane until reflex was lost and then exposed to $CO_2$ with 1% air. The spleen and the femur were isolated. The spleen was processed into a single cell suspension by homogenization and passage through 70 μm sieves. The marrow was isolated from the femur by centrifugation of the bone for 30 s at 3810 g and resuspended in FACS buffer (1× sterile PBS (pH 7.4), 2.5 mM ethylenediaminetetraacetic acid (EDTA), 0.05% (w/v) sodium azide ($NaN_3$), 2% (v/v) bovine serum albumin (BSA)).

After isolation, the spleen and bone marrow cells were stained. One million cells were counted using a ThermoFisher Countess II™ and added to a well of 96-well round bottom plates and the volume in each well was increased to 200 uL using FACS buffer. Cells were centrifuged at 484 g at 4° C. for 5 minutes and the liquid was discarded. Subsequently, cells were incubated with a solution containing the antibody for 45 minutes. The volume was increased to 200 μL and the cells were centrifuged at 484 g at 4° C. for 5 minutes and the liquid was discarded. A volume of 100 μL of propidium iodide (PI) was added at a 1:5,000 dilution (1 mg/mL stock) and the stained, single cells were introduced to a flow cytometer (Cytoflex™, Becman Coulter™). Single colour setups were used to generate the compensation matrix which was applied to all the samples.

The flow cytometry data was analyzed using FlowJo™ version 10 (Becton Dickension™ & Company (BD)). Corresponding immune cell subsets were identified based on the gating scheme shown in Table 2 and Table 3 above. The bar graphs for the percentage of eGFP positive ($eGFP^+$) cells and eGFP mean fluorescent intensity (MFI) were generated using Prism™ version 8 (GraphPad™) software. The gating schemes for the spleen and bone marrow are shown in Table 1 and Table 2 below.

Tissue Homogenate Assay

Tissues were removed from the mice and placed in 2 mL tubes and snap frozen in liquid nitrogen. The tissues were subsequently stored at −80° C. An appropriate volume of GLO™ lysis buffer from Promega™ was added to each of the tubes, ensuring that the samples remained frozen before addition of the lysis buffer. Samples were placed in a FastPrep™ homogenizer and the homogenizer was operated at a speed of 6 m/s for 20 seconds and repeated 2 times for a total of three rounds. The homogenized samples were spun down for 10 minutes at 12,000 rpm at room temperature and subsequently 50 μL of homogenate in duplicate was added to a black plate. The plate was transferred to a plate reader and the fluorescence was read at 640 nm excitation/720 nm emissions. Luminescence was determined by adding 50 μL of Steady Glo™ substrate into the homogenate sample and a luciferase signal was read.

Example 1

Extrahepatic mRNA Gene Expression in Immune Cell Subsets Increases Significantly Using High DSPC LNPs The effect of increasing the amount of DSPC from 10 mol % to 50 mol % in a four-component LNP containing enhanced green fluorescent protein mRNA ("eGFP mRNA") cargo was evaluated in vivo. As set out below, the LNP containing elevated levels of DSPC relative to the Onpattro™ formulation exhibited a significant increase (>>10%) in gene expression in macrophages, monocytes and/or T-cells from the spleen and/or bone marrow collected at both 24 hours and 3 days post-injection as compared to an Onpattro™-type formulation.

In particular, the following two four-component eGFP mRNA formulations (reported in mol %) comprising ionizable lipid, DSPC, cholesterol and PEG-lipid were compared in this example.

TABLE 1

Formulations examined in vivo containing eGFP mRNA

| Sample | Percent DSPC | Lipid composition/mol % |
|---|---|---|
| Onpattro ™ | 10 mol % | nMC3:DSPC:Chol:$PEG_{2000}$-DMG (50:10:38.5:1.5) |
| lcLNP ™ | 50 mol % | MF019:DSPC:Chol:$PEG_{2000}$-DMG (27.4:50:21.1:1.5) |

The DSPC content of the inventive 1cLNP™ of Table 1 was increased to 50 mol % at the expense of both ionizable lipid and cholesterol. The ionizable lipid included in the Onpattro™-like LNP was nor-MC3 (nMC3) as described in co-owned and co-pending WO 2022/246571 and the ionizable lipid in the inventive formulation comprising 50 mol % DSPC LNP was MF019 as described in WO 2022/155728A1 (each of which are incorporated herein by reference). The nitrogen-to-phosphate ratios (N/P) for the 10 mol % DSPC (Onpattro™-like LNP) and inventive mol % DSPC formulation (1cLNP™) were 6 and 9, respectively.

The Onpattro™-type formulation had a size of 38.4 nm, a polydispersity index (PDI) of and an entrapment efficiency of 88.4%. The inventive formulation (1cLNP™) containing mol % DSPC had a size of 78.9 nm, a PDI of 0.052 and an encapsulation efficiency of 64.4%.

In this example, flow cytometry was used to investigate the expression of eGFP mRNA in immune cell subsets of bone marrow and the spleen of C57BL/6J mice at various time points post-injection. The flow cytometry gating scheme of the spleen and bone marrow cells is shown in Tables 2 and 3 below.

TABLE 2

Gating scheme for the spleen
Gating on live immune ($CD45^+$) cells:

| Population in Spleen | Marker |
|---|---|
| Monocytes/macrophages | $CD19^-TCRb^-CD11b^+Ly6G^-$ |
| Neutrophils | $CD19^-TCRb^-CD11b^+Ly6G^+$ |
| B cells | $CD19^+$ |
| CD4 T cells | $TCRb^+CD4^+$ |
| CD8 T cells | $TCRb^+CD8^+$ |

TABLE 3

Gating scheme for the bone marrow
Gating on singlets:

| Population in Bone marrow | Marker |
|---|---|
| Erythroid* | $Ter119^+$ |
| B cells | $Ter119^-CD45^+CD19^+$ |
| T cells | $Ter119^-CD45^+TCRb^+$ |
| Monocytes/ macrophages | $Ter119^-CD45^+CD19^-TCRb^-CD11b^+Ly6G^-$ |
| Neutrophils | $Ter119^-CD45^+CD19^-TCRb^-CD11b^+Ly6G^+$ |

*After gating on erythroids, the live immune cells are gated as $CD45^+PI^-$ cells The results for the mRNA expression detected in the spleen sub-cell populations are presented in FIGS. 1A-F and FIGS. 2A-C.

The results for mRNA expression in bone marrow are shown in FIGS. 3A-F.

Figure 1B:
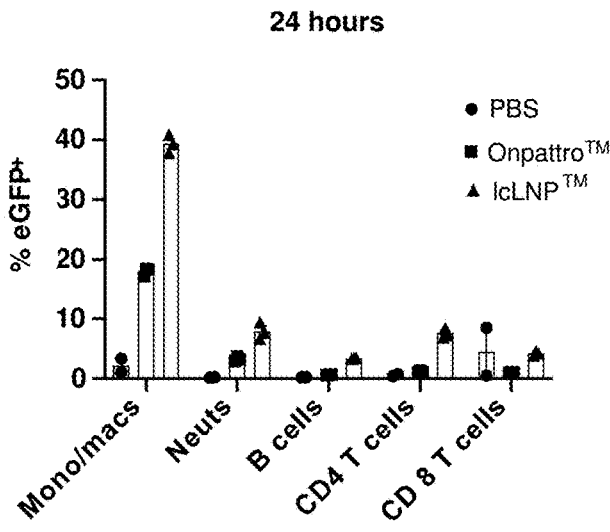
FIG. 1B shows the percentage of eGFP positive cells (% eGFP+) in the spleen of immune cell sub-populations as indicated (monocytes/macrophages, neutrophils, B cells, CD4 T cells and CD8 T cells) after 24 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or mol % DSPC (MF019:DSPC:Chol:PEG-lipid (27.4:50:21.1:1.5 mol:mol) ("1cLNP™")) to mice.
Figure 1C:
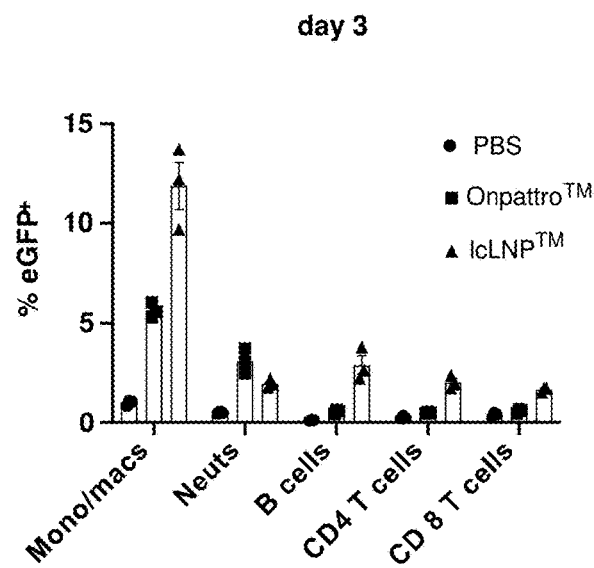
FIG. 1C shows the percentage of eGFP positive cells (% eGFP+) in the spleen of immune cell sub-populations as indicated (monocytes/macrophages, neutrophils, B cells, CD4 T cells and CD8 T cells) after 3 days post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or mol % DSPC (MF019:DSPC:Chol:PEG-lipid (27.4:50:21.1:1.5 mol:mol) ("1cLNP™")) to mice.
Figure 1D:
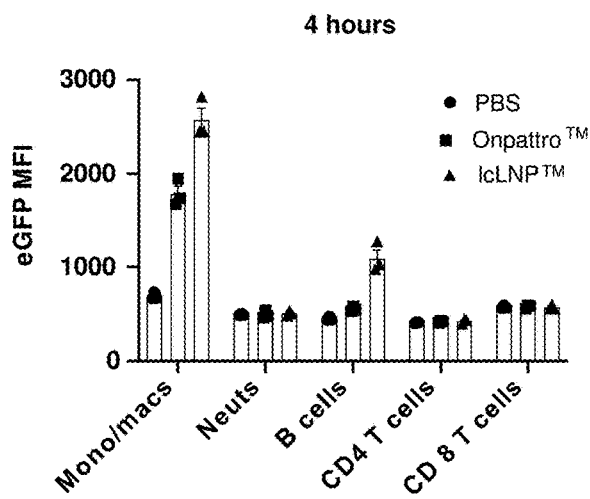
FIG. 1D shows the mean fluorescent intensity (MFI) in the spleen of immune cell sub-populations as indicated (monocytes/macrophages, neutrophils, B cells, CD4 T cells and CD8 T cells) after 4 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.

As can be seen, the results in FIGS. 1A-C show that at 4 hours, 24 hours and 3 days, the monocyte and macrophage sub-populations in the spleen of mice treated with the GFP mRNA-containing 1cLNP™ having 50 mol % DSPC exhibited an increase of 20% or more of cells positive for GFP over the Onpattro™ formulation having only 10 mol % DSPC. Similar results were observed at the same time points when the data was plotted using the measured MFI of the GFP (FIGS. 1D-F).

Figure 1E:
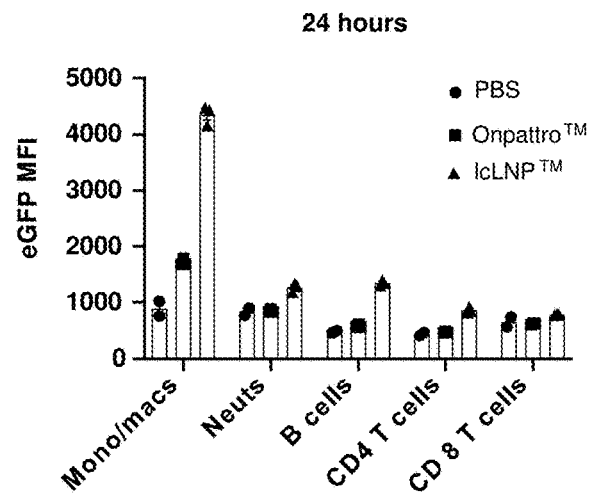
FIG. 1E shows the MFI in the spleen of immune cell sub-populations as indicated (monocytes/macrophages, neutrophils, B cells, CD4 T cells and CD8 T cells) after 24 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 1F:
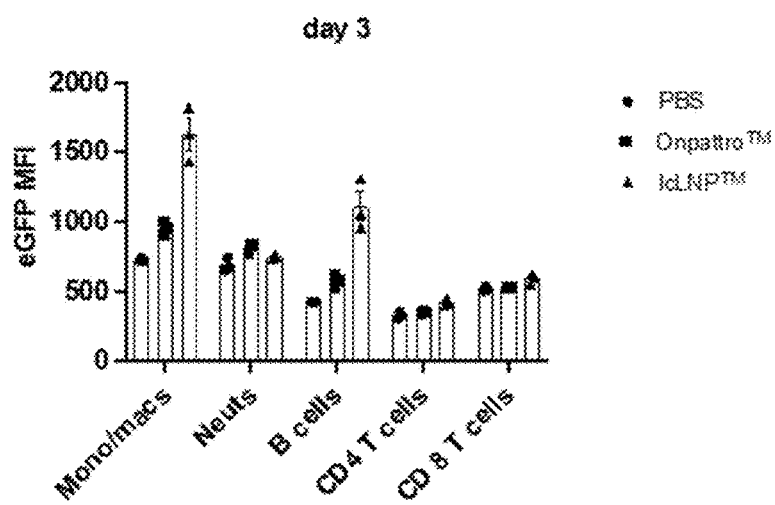
FIG. 1F show the MFI in the spleen of immune cell sub-populations as indicated (monocytes/macrophages, neutrophils, B cells, CD4 T cells and CD8 T cells) after 3 days post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 2A:
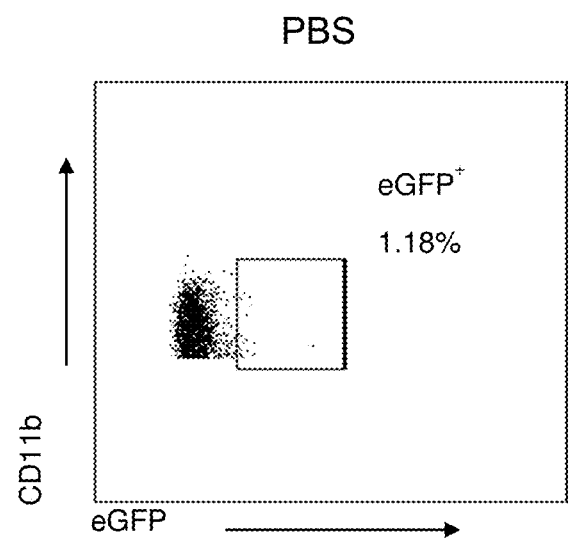
FIG. 2A shows a representative scatter plot depicting the percentage of eGFP monocytes/macrophages in the spleen at 24 hours post-injection of phosphate buffered saline (PBS) to mice.
Figure 2B:
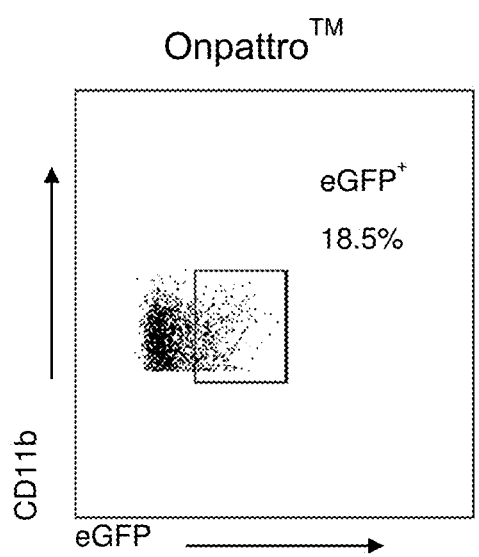
FIG. 2B shows a representative scatter plot depicting the percentage of eGFP monocytes/macrophages in the spleen at 24 hours post-injection of eGFP-mRNA LNPs having 10 mol % DSPC (nMC3:DSPC:Chol:PEG-lipid (50:10:38.5:1.5) ("Onpattro™")) to mice.
Figure 2C:
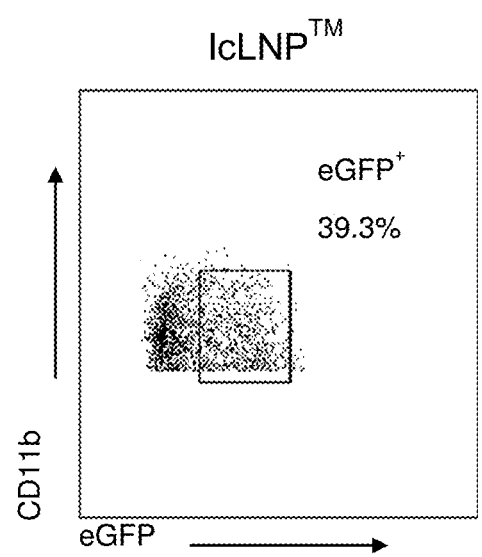
FIG. 2C shows a representative scatter plot depicting the percentage of eGFP monocytes/macrophages in the spleen at 24 hours post-injection of eGFP-mRNA LNPs 50 mol % DSPC (MF019:DSPC:Chol:PEG-lipid (27.4:50:21.1:1.5 mol:mol) ("1cLNP™")) to mice.

FIGS. 2A-2C show representative scatter plots depicting the eGFP expression levels of the monocyte/macrophage cell populations at a single cell resolution in the spleen at 24 hours post-injection for the data shown in FIGS. 1B and 1E. As can be better visualized, the mRNA-1cLNP™ comprising 50 mol % DSPC had significantly more eGFP cells than mRNA-Onpattro™. The eGFP cells were two-fold greater for the mRNA-1cLNP™ over mRNA-Onpattro™. (The number of cells positive for eGFP was 18.5% for Onpattro™ and 39.3% for 1cLNP™).

Figure 3A:
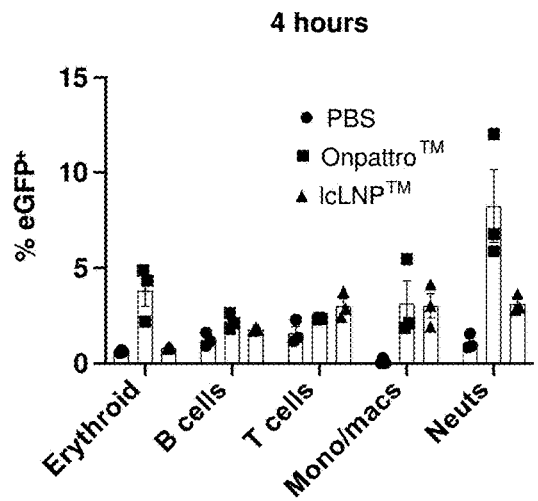
FIG. 3A show the percentage of eGFP positive cells (% eGFP+) in the bone marrow of immune cell sub-populations as indicated (erythroid, B cells, T cells, monocytes/macrophages and neutrophils) after 4 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 3B:
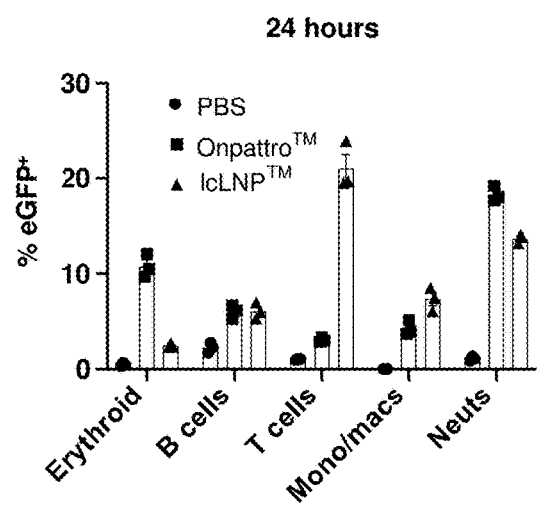
FIG. 3B show the percentage of eGFP positive cells (% eGFP+) in the bone marrow of immune cell sub-populations as indicated (erythroid, B cells, T cells, monocytes/macrophages and neutrophils) 24 hours post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 3C:
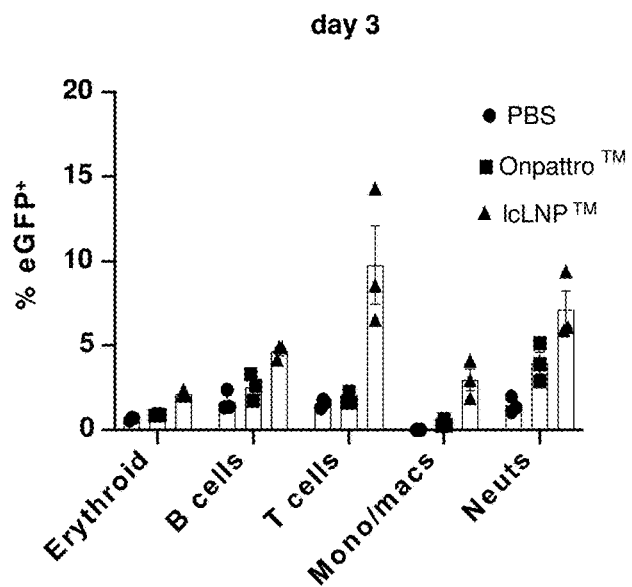
FIG. 3C shows the percentage of eGFP positive cells (% eGFP+) in the bone marrow of immune cell sub-populations as indicated (erythroid, B cells, T cells, monocytes/macrophages and neutrophils) after 3 days post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or mol % DSPC (MF019:DSPC:Chol:PEG-lipid (27.4:50:21.1:1.5 mol:mol) ("1cLNP™")) to mice.
Figure 3D:
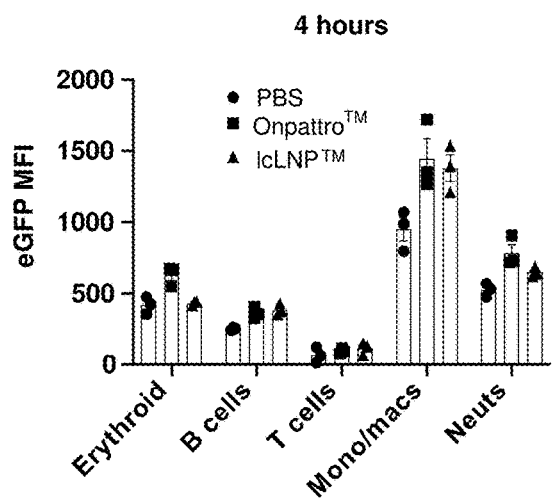
FIG. 3D shows the mean fluorescent intensity (MFI) in the bone marrow of immune cell sub-populations as indicated (erythroid, B cells, T cells, monocytes/macrophages and neutrophils) after 4 hours post-injection of phosphate buffered saline (PBS); and eGFP-mRNA LNPs having mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 3E:
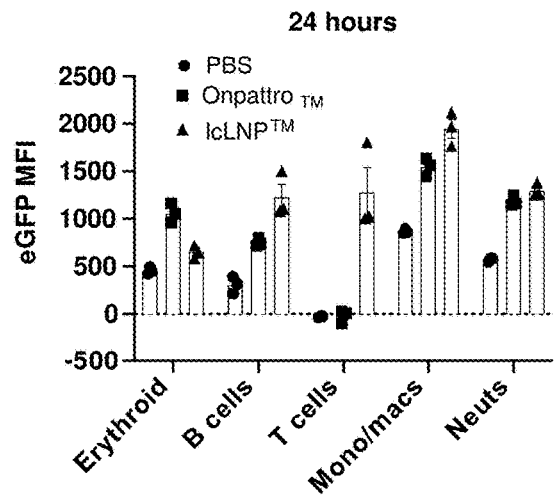
FIG. 3E shows the mean fluorescent intensity (MFI) in the bone marrow of immune cell sub-populations as indicated (erythroid, B cells, T cells, monocytes/macrophages and neutrophils) after 24 hours post-injection of phosphate buffered saline (PBS); and eGFP-mRNA LNPs having mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.
Figure 3F:
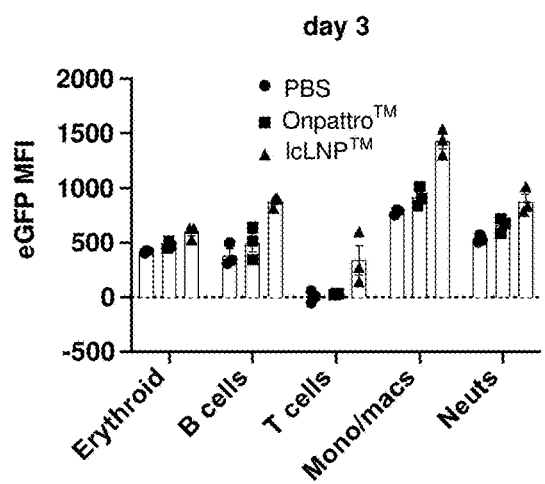
FIG. 3F show the MFI in the bone marrow of immune cell sub-populations as indicated (erythroid, B cells, T cells, monocytes/macrophages and neutrophils) after 3 days post-injection of phosphate buffered saline (PBS); and eGFP-mRNA LNPs having 10 mol % DSPC (nMC3:DSPC:Chol:PEG-lipid (50:10:38.5:1.5) ("Onpattro™")); or 50 mol % DSPC (MF019:DSPC:Chol:PEG-lipid (27.4:50:21.1:1.5 mol:mol) ("1cLNP™")) to mice.

Similarly, FIGS. 3A-C show that in the bone marrow at 24 hours and 3 days post-injection, the monocyte and macrophage sub-populations of mice treated with the mRNA-1cLNP having 50 mol % DSPC exhibited an increase of 20% or more of cells that were positive for green fluorescent protein (GFP±cells) over the Onpattro™ formulation. Similar results were observed at 24 hours and 3 days when the data was plotted using the measured MFI of the GFP (FIGS. 3D-F). In addition, T-cell sub-populations in the bone marrow of mice treated with the mRNA-1cLNP having 50 mol % DSPC exhibited an increase of 20% or more of cells that were positive for green fluorescent protein (GFP$^+$ cells) over the Onpattro™ formulation at time points greater than 24 hours (FIGS. 3B, 3C, 3E and 3F).

Figure 4A:
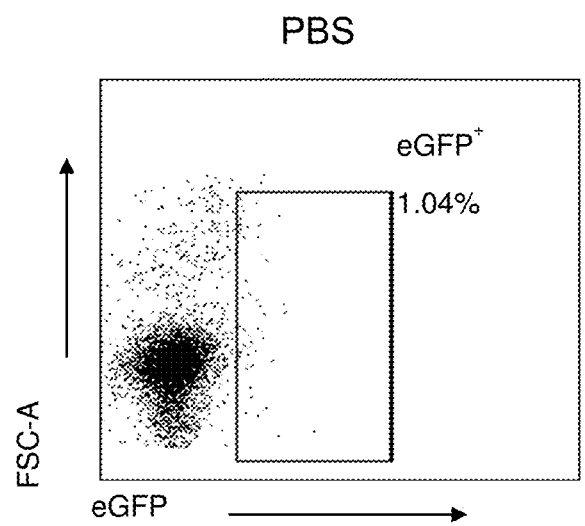
FIG. 4A shows a representative scatter plot depicting the percentage of eGFP T cells in the bone marrow at 24 hours post-injection of phosphate buffered saline (PBS) to mice.
Figure 4B:
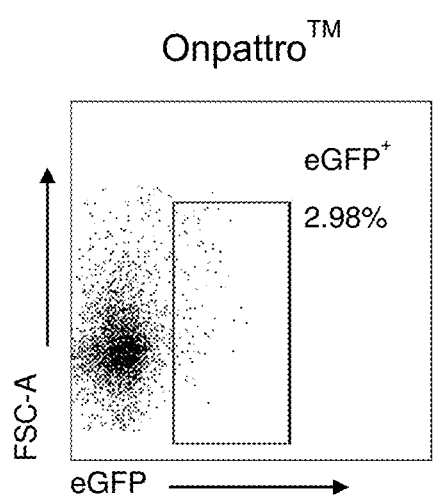
FIG. 4B shows the representative scatter plots depicting the percentage of eGFP T cells in the bone marrow at 24 hours post-injection of eGFP-mRNA LNPs having 10 mol % DSPC (nMC3:DSPC:Chol:PEG-lipid (50:10:38.5:1.5) ("Onpattro™") to mice.
Figure 4C:
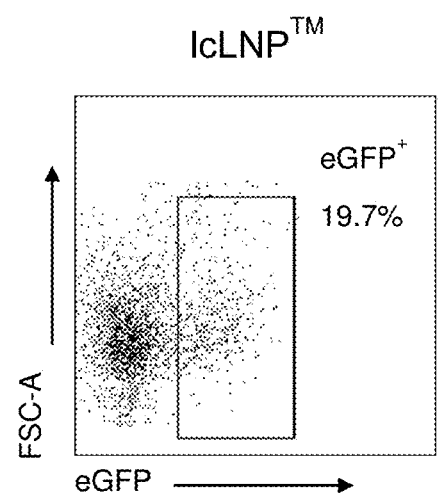
FIG. 4C show the representative scatter plots depicting the percentage of eGFP T cells in the bone marrow at 24 hours post-injection of eGFP-mRNA LNPs having 50 mol % DSPC (MF019:DSPC:Chol:PEG-lipid (27.4:50:21.1:1.5 mol:mol) ("1cLNP™")) to mice.

FIGS. 4A-4C show representative scatter plots depicting the eGFP expression levels of the T cell populations at a single cell resolution in the bone marrow at 24 hours post-injection for the data shown in FIGS. 3B and 3E. As can be better visualized, in the T cell population at 24 hours, the eGFP$^+$ cells were five-fold greater for the mRNA-1cLNP™ relative to the mRNA-Onpattro™. (The number of cells positive for eGFP was 2.98% for Onpattro™ and 19.5% for 1cLNP™ having 50 mol % DSPC).

Example 2 mRNA Gene Expression in Immune Cell Subsets Increases Significantly Using High DSPC LNPs Incorporating a Variety Of Ionizable Lipids Example 1 demonstrates that increasing DSPC content in a four-component mRNA-LNP system comprising an ionizable sulfur lipid, MF019, results in significant increases in extrahepatic mRNA expression. To examine the effect of increasing DSPC in a four-component LNP system containing a different ionizable lipid, the same formulations as in Example 1 were examined for mRNA gene expression in the spleen and bone marrow, but instead incorporated the ionizable lipid, MC3 (DLin-MC3-DMA).

As discussed below, similar trends in mRNA expression in bone marrow and spleen were observed as the DSPC content increased but in which the ionizable lipid in the formulations was MC3.

The following two four-component eGFP mRNA formulations comprising MC3 ionizable lipid, DSPC, cholesterol and PEG-lipid were compared.

TABLE 4

| MC3 ionizable lipid formulations examined in vivo containing eGFP mRNA | | |
|---|---|---|
| Sample | Percent DSPC | Lipid composition/mol % |
| Onpattro ™ | 10 mol % | MC3:DSPC:Chol:PEG$_{2000}$-DMG (50:10:38.5:1.5)* |
| lcLNP ™ | 50 mol % | MC3:DSPC:Chol:PEG$_{2000}$-DMG (27.4:50:21.1:1.5) |

*MC3 is the ionizable lipid, DLin-MC3-DMA

Figure 5A:
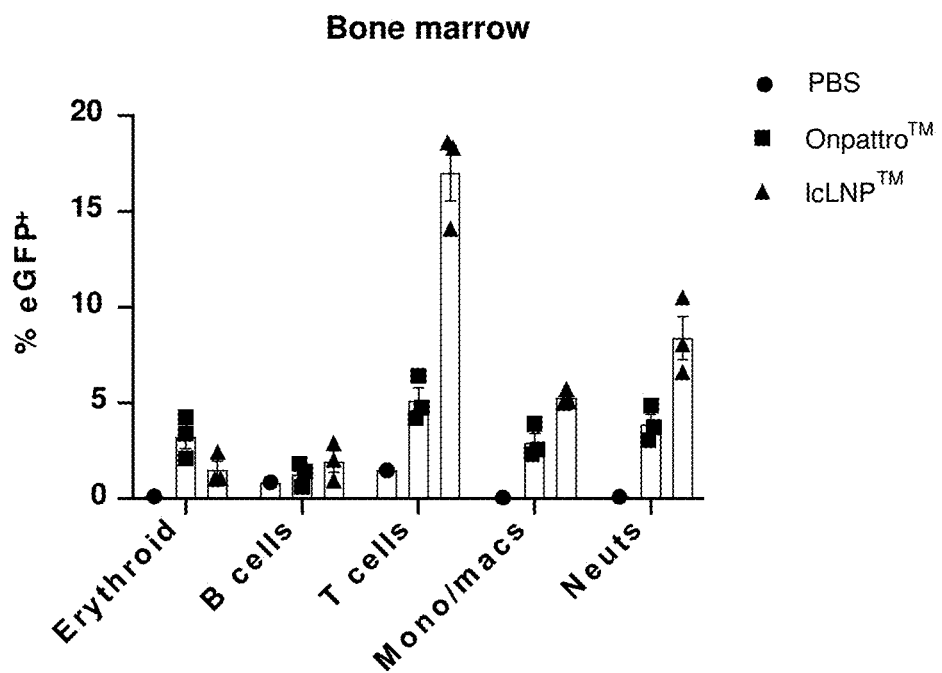
FIG. 5A shows the percentage of enhanced green fluorescent protein (eGFP) positive cells (% eGFP+) in the bone marrow of immune cell sub-populations as indicated (erythroid, B cells, T cells, monocytes/macrophages and neutrophils) after 24 hours post-injection of phosphate buffered saline (PBS); and eGFP-mRNA LNPs having 10 mol % DSPC (MC3:DSPC:Chol:PEG-lipid (50:10:38.5:1.5) ("Onpattro™")); or 50 mol % DSPC (MC3:DSPC:Chol:PEG-lipid (27.4:50:21.1:1.5 mol:mol) ("1cLNP™")) to mice. MC3 is an ionizable cationic amino lipid as described herein.

As can be seen, the bar graph in FIG. 5A shows that at 24 hours, the T cell, monocyte and macrophage sub-populations and neutrophils in the bone marrow of mice treated with the GFP mRNA-containing lcLNP™ having 50 mol % DSPC exhibited an increase of 20% or more of cells positive for GFP over the Onpattro™ formulation having only 10 mol % DSPC. The same general trends were observed when the data was plotted using the measured MFI of the GFP (FIG. 5B).

Figure 5B:
FIG. 5B shows the mean fluorescent intensity (MFI) in the bone marrow of immune cell sub-populations as indicated (erythroid, B cells, T cells, monocytes/macrophages and neutrophils) after 24 hours post-injection of phosphate buffered saline (PBS); and eGFP-mRNA LNPs having 10 mol % DSPC (MC3:DSPC:Chol:PEG-lipid (50:10:38.5:1.5) ("Onpattro™")); or 50 mol % DSPC (MC3:DSPC:Chol:PEG-lipid (27.4:50:21.1:1.5 mol:mol) ("1cLNP™")) to mice.

FIGS. 6A-6C show representative scatter plots depicting the eGFP expression levels of the T-cell populations at a single cell resolution in the bone marrow for the data shown in FIGS. 5A and 5B. As can be better visualized, the mRNA-1cLNP™ comprising 50 mol % DSPC (FIG. 6C) had significantly more eGFP positive cells than mRNA-Onpattro™ LNP (FIG. 6B). The eGFP positive cells were at least four-fold greater for the mRNA-1cLNP™ over mRNA-Onpattro™ (FIG. 6B shows that only 4.75% of the cells were positive for eGFP vs. 18.3% in FIG. 6C).

Figure 7:
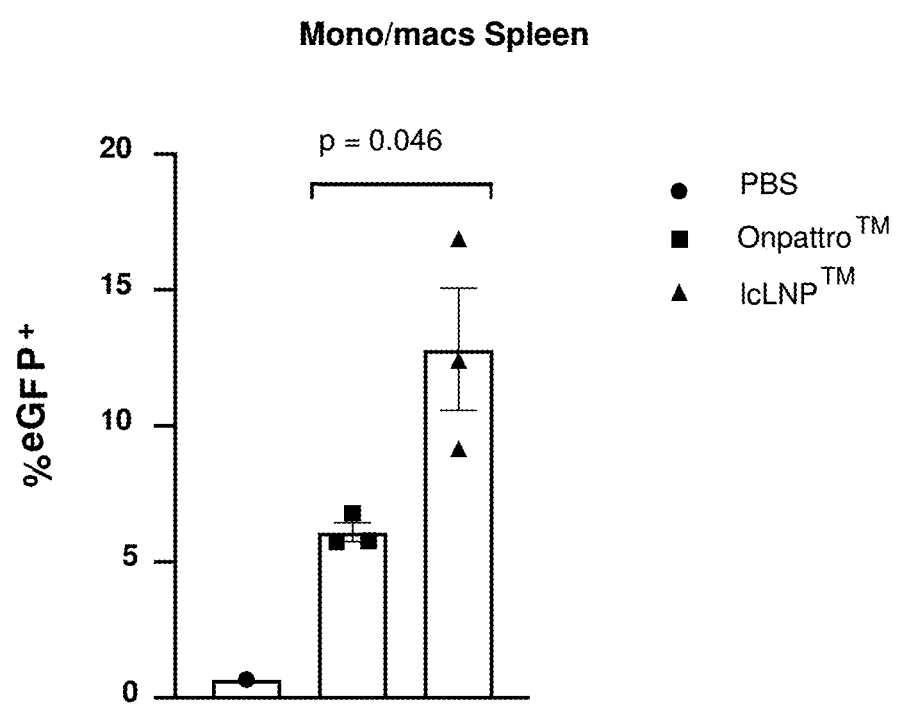
FIG. 7 shows the percentage of enhanced green fluorescent protein (eGFP) positive cells (% eGFP+) in the spleen of monocytes/macrophages after 24 hours post-injection of phosphate buffered saline (PBS); and eGFP-mRNA LNPs having 10 mol % DSPC (MC3:DSPC:Chol:PEG-lipid (50: 10:38.5:1.5 mol:mol) ("Onpattro™")); or 50 mol % DSPC (MC3:DSPC:Chol:PEG-lipid (27.4:50:21.1:1.5 mol:mol) ("1cLNP")) to mice.

FIG. 7 is a bar graph showing that at 24 hours, the monocyte and macrophage (mono/macs) sub-populations in the spleen of mice treated with the GFP mRNA-containing 1cLNP™ having 50 mol % DSPC exhibited an increase of about 2-fold more cells positive for GFP than the Onpattro™ formulation having only 10 mol % DSPC.

FIGS. 8A-8C show representative scatter plots depicting the eGFP expression levels of the monocyte/macrophage cell populations at a single cell resolution in the spleen for the data shown in FIG. 7. The mRNA-1cLNP™ comprising 50 mol % DSPC (FIG. 8C) had significantly more eGFP positive cells than mRNA-Onpattro™ (FIG. 8B). The eGFP positive cells were at least two-fold greater for the mRNA-1cLNP™ over mRNA-Onpattro™. (In FIG. 8B, 5.78% of the cells were positive, while in FIG. 8C 12.4% were positive for eGFP).

Example 3 mRNA Gene Expression in Immune Cell Subsets Increases Significantly Using High DSPC LNPs but Not for Sphingomyelin The effect of increasing the content of another neutral lipid, egg sphingomyelin (ESM), on in vivo mRNA expression was assessed using formulations that were the same as those in Examples 1 and 2 but that replaced the DSPC with ESM. Surprisingly, the increases in mRNA expression in the extrahepatic tissues for high DSPC LNPs were not observed with LNPs having elevated levels of ESM.

The formulations examined are shown in Table 5 below.

TABLE 5

Formulations examined in vivo containing eGFP mRNA

| Sample | Mole percent/ neutral lipid | Lipid composition/mol % |
|---|---|---|
| lcLNP ™ | 50 mol % DSPC | MC3:DSPC:Chol:PEG$_{2000}$-DMG (27.4:50:21.1:1.5) |
| ESM | 50 mol % ESM | MC3:ESM:Chol:PEG$_{2000}$-DMG (27.4:50:21.1:1.5) |

Figure 9A:
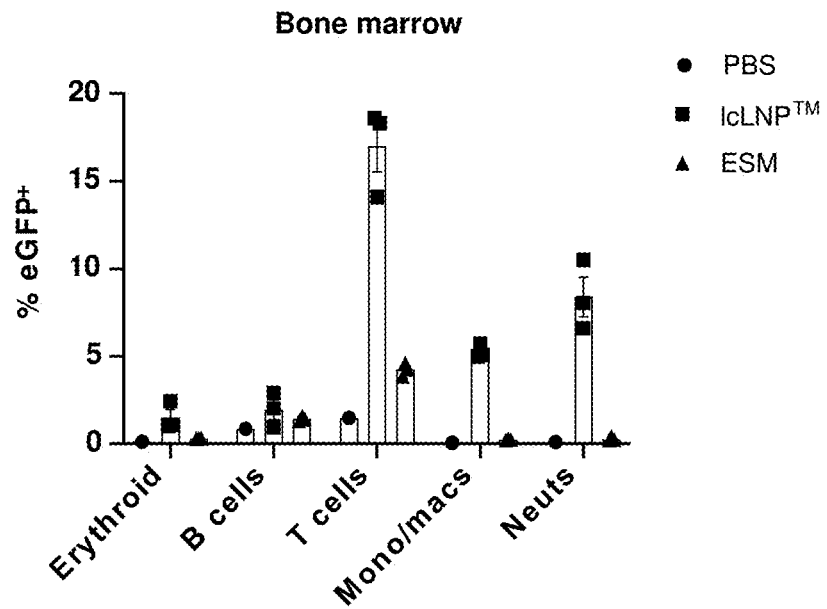
FIG. 9A shows the percentage of enhanced green fluorescent protein (eGFP) positive cells (% eGFP) in the bone marrow of immune cell sub-populations as indicated (erythroid, B cells, T cells, monocytes/macrophages and neutrophils) after 24 hours post-injection of phosphate buffered saline (PBS); and eGFP-mRNA LNPs having 50 mol % DSPC (MC3:DSPC:Chol:PEG-lipid (27.4:50:21.1:1.5 mol: mol) ("1cLNP")) or having 50 mol % egg sphingomyelin (ESM) (MC3:ESM:Chol:PEG-lipid (27.4:50:21.1:1.5 mol: mol) to mice.

As can be seen, the bar graphs in FIG. 9A show that at 24 hours post-injection, the cell sub-populations in the bone marrow (erythroids, B cells, T cells, monocytes/macrophages and neutrophils) of mice treated with the GFP mRNA-containing 1cLNP™ having 50 mol % DSPC exhibited an increase of >>20% or more of cells positive for GFP in most cell types measured over the same formulation having egg sphingomyelin (ESM) as the neutral lipid. Similar general trends were observed when the data was plotted using the measured MFI of the GFP (FIG. 9B).

Figure 9B:
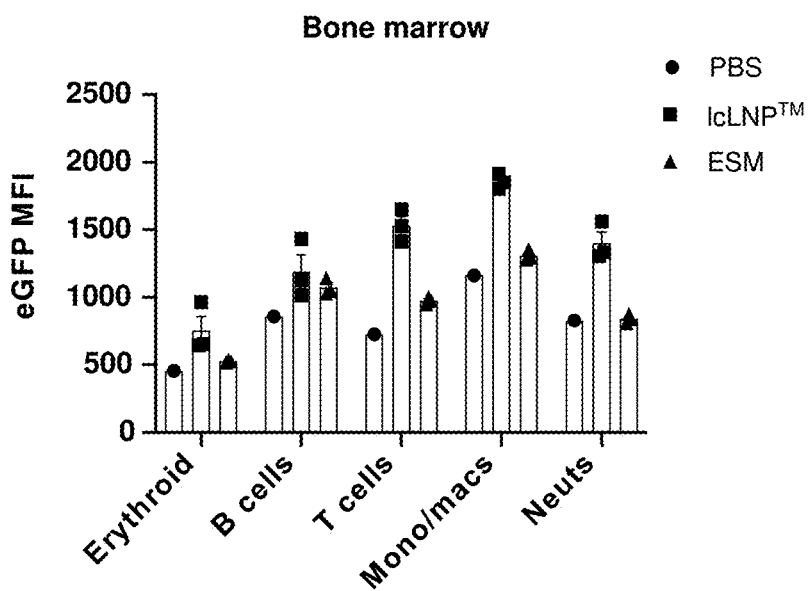
FIG. 9B shows the mean fluorescent intensity (MFI) in the bone marrow of immune cell sub-populations as indicated (erythroid, B cells, T cells, monocytes/macrophages and neutrophils) after 24 hours post-injection of phosphate buffered saline (PBS); and eGFP-mRNA LNPs having mol % DSPC (MC3:DSPC:Chol:PEG-lipid (27.4:50:21.1:1.5 mol: mol) ("1cLNP")) or having mol % egg sphingomyelin (ESM) (MC3:ESM:Chol:PEG-lipid (27.4:50:21.1:1.5 mol: mol) to mice.
Figure 10A:
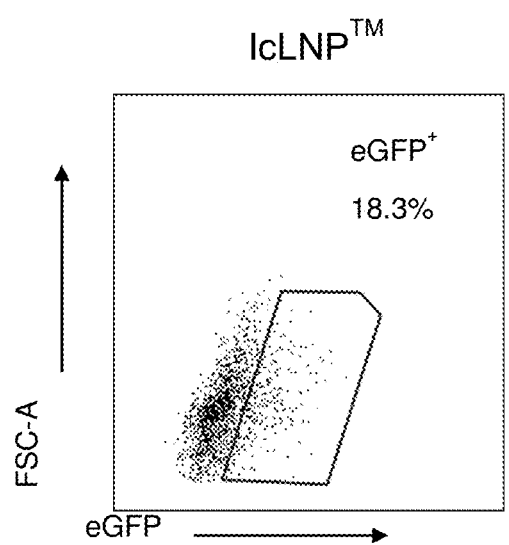
FIG. 10A shows a representative scatter plot depicting the percentage of eGFP T cells in the bone marrow at 24 hours post-injection of eGFP-mRNA LNPs having 50 mol % DSPC (MC3:DSPC:Chol:PEG-lipid (50:10:38.5:1.5) ("1cLNP™")) to mice.
Figure 10B:
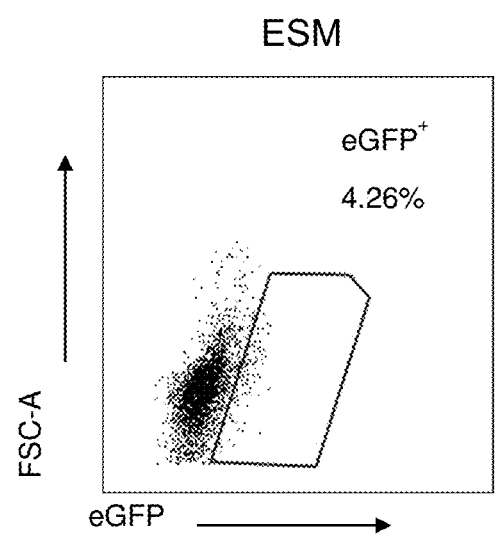
FIG. 10B shows a representative scatter plot depicting the percentage of eGFP T cells in the bone marrow at 24 hours post-injection of eGFP-mRNA LNPs having 50 mol % ESM (MC3:ESM:Chol:PEG-lipid (27.4:50:21.1:1.5 mol:mol) ("ESM"

FIGS. 10A and 10B show representative scatter plots depicting the eGFP expression levels of the T-cell populations at a single cell resolution in the bone marrow for the data shown in FIGS. 9A and 9B. As can be better visualized, the mRNA-1cLNP™ comprising 50 mol % DSPC (FIG. 10A) had about 4 times more eGFP positive cells than the egg sphingomyelin (ESM) formulation (FIG. 10B) (the eGFP$^+$ was 18.3 for the 1cLNP™ and only 4.26 for the ESM LNPs).

Figure 11A:
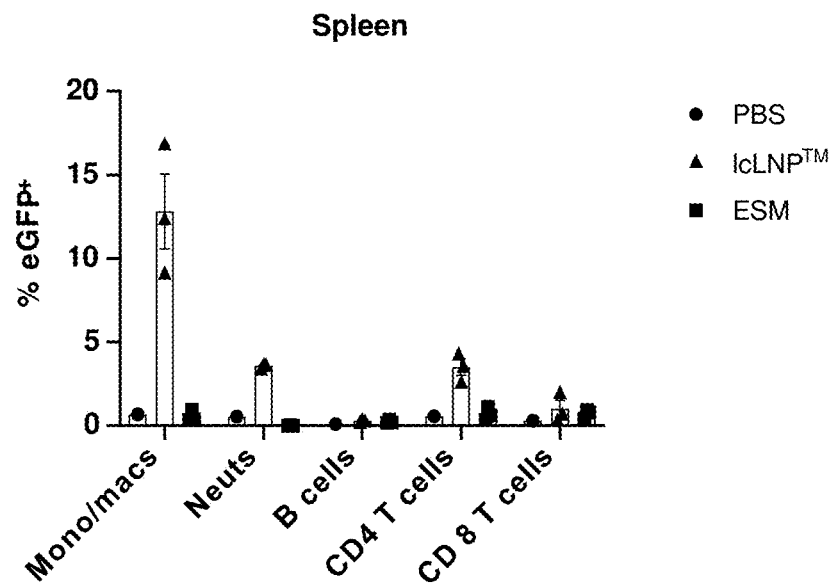
FIG. 11A shows the percentage of enhanced green fluorescent protein (eGFP) positive cells (% eGFP+) in the spleen of immune cell sub-populations as indicated (monocytes/macrophages, neutrophils, B cells, CD4 T cells and CD8 T cells) after 24 hours post-injection of phosphate buffered saline (PBS); and eGFP-mRNA LNPs having 50 mol % DSPC (MC3:DSPC:Chol:PEG-lipid (27.4:50:21.1: 1.5 mol:mol) ("1cLNP")) or having 50 mol % egg sphingomyelin (ESM) (MC3:ESM:Chol:PEG-lipid (27.4:50: 21.1:1.5 mol:mol) to mice.

FIG. 11A is a bar graph showing that at 24 hours, various sub-populations in the spleen of mice treated with the GFP mRNA-containing 1cLNP™ having 50 mol % DSPC exhibited an increase of cells positive for GFP over the overwise same formulation containing ESM.

Figure 11B:
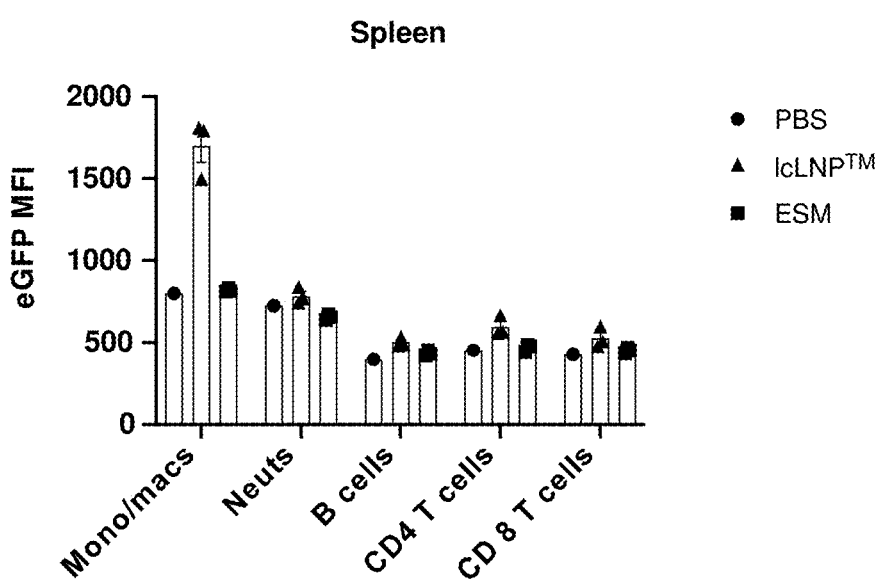
FIG. 11B shows the mean fluorescent intensity (MFI) in the spleen of immune cell sub-populations as indicated (monocytes/macrophages, neutrophils, B cells, CD4 T cells and CD8 T cells) after 24 hours post-injection of phosphate buffered saline (PBS); and eGFP-mRNA LNPs having 50 mol % DSPC (MC3:DSPC:Chol:PEG-lipid (27.4:50:21.1: 1.5 mol:mol) ("1cLNP")) or having 50 mol % egg sphingomyelin (ESM) (MC3:ESM:Chol:PEG-lipid (27.4:50: 21.1:1.5 mol:mol) to mice.

The increase in cells positive for EGF mRNA in monocytes and macrophages was about 6-fold more for the DSPC LNPs relative to the ESM LNPs (FIG. 11A). The same general trends were observed when the same data was plotted showing mean fluorescent intensity (MFI; FIG. 11B).

Figure 12A:
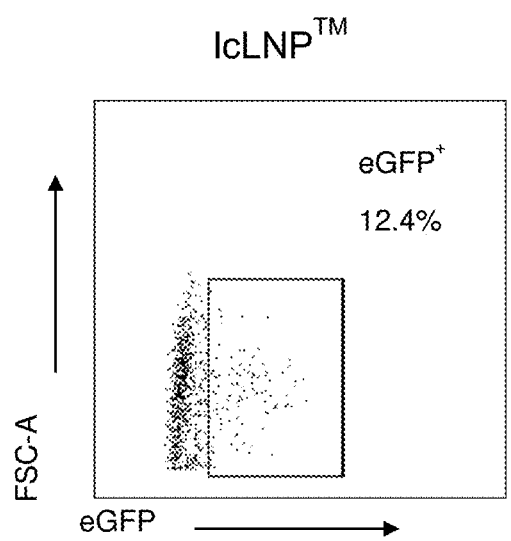
FIG. 12A shows a representative scatter plot depicting the percentage of eGFP macrophages/monocytes in the spleen at 24 hours post-injection of eGFP-mRNA LNPs having 50 mol % DSPC (MC3:DSPC:Chol:PEG-lipid (50:10:38.5:1.5) ("1cLNP™")) to mice.
Figure 12B:
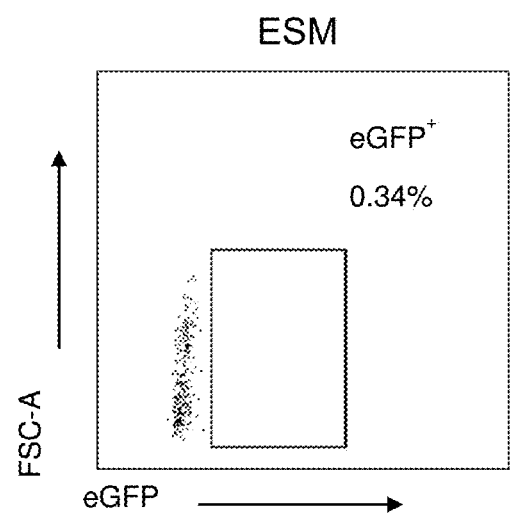
FIG. 12B shows a representative scatter plot depicting the percentage of eGFP macrophages/monocytes in the spleen at 24 hours post-injection of eGFP-mRNA LNPs having 50 mol % ESM (MC3:ESM:Chol:PEG-lipid (27.4:50:21.1:1.5 mol:mol) ("ESM")) to mice.

FIGS. 12A and 12B show representative scatter plots depicting the eGFP expression levels of the monocyte/macrophage cell populations at a single cell resolution in the spleen for the data shown in FIG. 11. The mRNA-1cLNP™ comprising 50 mol % DSPC (FIG. 12A) had significantly more eGFP positive cells than the same formulation in which DSPC was replaced with egg sphingomyelin (FIG. 12B). The eGFP positive cells were at least 20-fold greater for the mRNA-1cLNP™ comprising DSPC over the ESM LNPs.

Example 4 mRNA Gene Expression Increases Significantly Using High DSPC LNPs in a Variety or Tissues and Organs and Reduces Liver Toxicity This example demonstrates that LNPs with elevated levels of DSPC exhibit increased expression of mRNA in the spleen, lungs, kidney, heart, bone marrow, abdomen, back and ear relative to an Onpattro™-type formulation 24 hours after injection.

The LNPs in Table 6 below were examined.

TABLE 6

LNPs examined for expression in the liver, spleen, lungs, kidney, heart, bone marrow, abdomen, back and ear relative to an Onpattro ™-type formulation

| LNP | DSPC mol % | Lipid composition/mol % |
|---|---|---|
| Onpattro ™ (nMC3) | 10 | nMC3:DSPC:Chol:PEG$_{2000}$-DMG (50:10:38.5:1.5) |
| lcLNP ™ (MF019) | 50 | MF019:DSPC:Chol:PEG$_{2000}$-DMG (27.4:50:21.1:1.5) |
| lcLNP ™ (NTx-C16) | 50 | NTx-C16:DSPC:Chol:PEG$_{2000}$-DMG (27.4:50:21.1:1.5) |

The N/P for each formulation was 9 and the control was phosphate buffered saline (PBS). The mRNA encodes for luciferase and the LNPs were administered to CD-1 mice at 1 mg/kg and 5 mg/kg and tissue homogenates were quantified for luciferase at 24 hours post-administration. The ionizable cationic lipid MF019 is described in WO 2022/155728A1. The ionizable cationic lipid, NTx-C16, has the following structure:

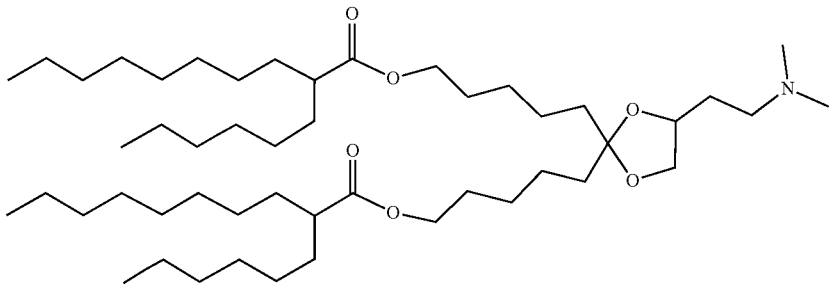 [SMILES: CCCCCCCCC(CCCCCCC)C(=O)OCCCCCC1(CCCCCOC(=O)C(CCCCCCC)CCCCCCCC)OCC(CCN(C)C)O1]

Figure 13A:
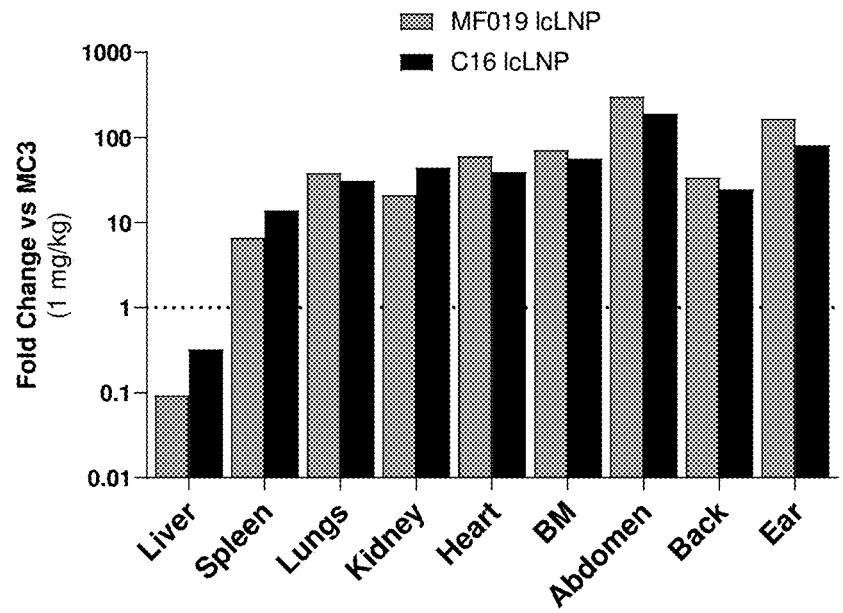
FIG. 13A shows fold-change of luminescence for mRNA-LNPs MF019:DSPC: Chol:PEG2000-DMG (27.4:50:21.1: 1.5 mol:mol) and NTx-C16:DSPC:Chol:PEG2000-DMG (27.4:50:21.1:1.5 mol:mol) vs Onpattro™ nMC3:DSPC: Chol:PEG 2000-DMG (50:10:38.5:1.5 mol:mol) at a dose of 1 mg/kg administered to CD-1 mice. The mRNA expression at 24 hours post-injection was quantified in the liver, spleen, lungs, kidney, heart, bone marrow (BM), abdomen, back and ear by measuring luminescence.
Figure 13B:
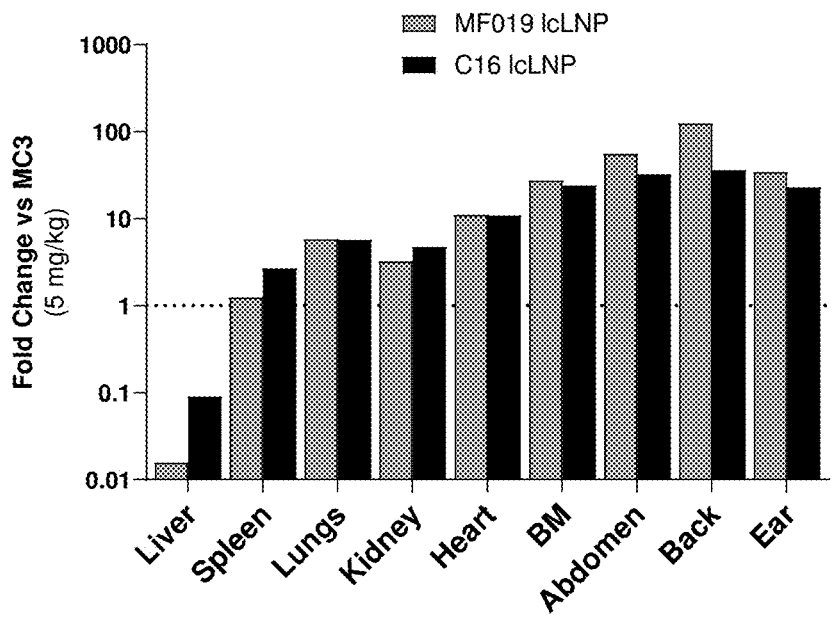
FIG. 13B shows fold-change of luminescence for mRNA-LNPs MF019:DSPC: Chol:PEG2000-DMG (27.4:50:21.1: 1.5 mol:mol) and NTx-C16:DSPC:Chol:PEG2000-DMG (27.4:50:21.1:1.5 mol:mol) vs Onpattro™ nMC3:DSPC: Chol:PEG2000-DMG (50:10:38.5:1.5 mol:mol) at a dose of 5 mg/kg administered to CD-1 mice. The mRNA expression at 24 hours post-injection was quantified in the liver, spleen, lungs, kidney, heart, bone marrow (BM), abdomen, back and ear by measuring luminescence.

FIGS. 13A and 13B show that the fold change for 1cLNP™ samples with above 50 mol % DSPC vs an Onpattro™-type formulation having 10 mol % DSPC was greater than 1 for each extrahepatic organ examined at both doses of 1 mg/kg and 5 mg/kg respectively.

Figure 13C:
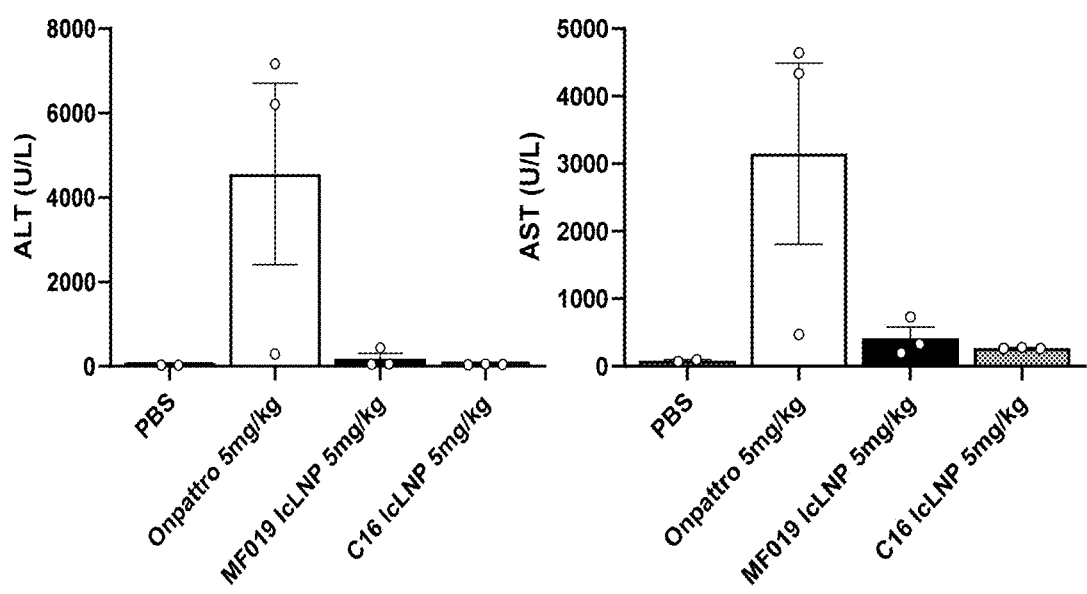
FIG. 13C shows the serum activity (U/L) of alanine transaminase (ALT) (left) and aspartate transaminase (AST) (right) 24 hours after CD-1 mice were injected at a dose of 5 mg/kg LNP-mRNA encoding luciferase. The LNPs were Onpattro™ (nMC3:DSPC:Chol:PEG2000-DMG (50:10: 38.5:1.5 mol:mol)) and mRNA-LNPs MF019:DSPC: Chol: PEG2000-DMG (27.4:50:21.1:1.5 mol:mol) and NTx-C16: DSPC:Chol:PEG2000-DMG (27.4:50:21.1:1.5 mol:mol).

FIG. 13C shows the serum activity (U/L) of enzymes correlated with liver toxicity for the 1cLNP™ samples of Table 6 above and Onpattro™. In particular, the figures show the levels of liver serum enzymes alanine transaminase (ALT) (left) and aspartate transaminase (AST) (right) 24 hours after CD-1 mice were injected at a dose of 5 mg/kg LNP-mRNA encoding luciferase. Both ALT and AST activity (U/L) were elevated in the serum after injection of Onpattro™ (nMC3) but their activities were comparatively lower after injection of both 1cLNP™ samples having 50 mol % DSPC. ALT and AST are markers of liver toxicity and thus demonstrate that LNPs with elevated phosphatidylcholine have a reduced toxicity in the liver relative to Onpattro™.

Example 5 mRNA Gene Expression of LNPs Having Elevated Levels of Various Phosphatidylcholine Lipids The following in vivo data demonstrate that LNPs with elevated levels of various phosphatidylcholine lipids exhibit increased expression of mRNA in the spleen, heart, lung, kidney, muscle tissue, bone marrow (BM) and ear relative to an Onpattro™-type formulation.

The following mRNA-LNPs were prepared with elevated levels of DSPC, DOPC, POPC, DPPC and combinations of DSPC and DOPC at various mol ratios as set forth in Table 7 below.

TABLE 7

LNPs prepared with different phosphatidylcholine lipids examined for extrahepatic expression

| LNP | Ionizable cationic lipid mol % | Phosphatidylcholine mol % | Chol mol % | PEG-DMG mol % | N/P |
|---|---|---|---|---|---|
| A | 50 nMC3 | 10 DSPC | 38.5 | 1.5 | 6 |
| B | 27.4 nMC3 | 50 DSPC | 21.1 | 1.5 | 9 |
| C | 27.4 C-109 | 50 DSPC | 21.1 | 1.5 | 9 |
| D | 27.4 C-109 | 50 DOPC | 21.1 | 1.5 | 9 |
| E | 27.4 C-109 | 50 POPC | 21.1 | 1.5 | 9 |
| F | 27.4 C-109 | 50 DPPC | 21.1 | 1.5 | 9 |
| G | 27.4 C-109 | 40:10 DSPC:DOPC | 21.1 | 1.5 | 9 |
| H | 27.4 C-109 | 30:20 DSPC:DOPC | 21.1 | 1.5 | 9 |
| I | 27.4 C-109 | 20:30 DSPC:DOPC | 21.1 | 1.5 | 9 |
| J | 27.4 C-109 | 10:40 DSPC:DOPC | 21.1 | 1.5 | 9 |

The mRNA encodes for luciferase and the N/P for each formulation is indicated below. Tissue homogenate luciferase levels were measured in CD-1 mice as previously indicated at 24 hours post-injection. The ionizable cationic lipid nMC3 is described in as described in co-owned and co-pending WO 2022/246571 and C-109 ionizable lipid is described in U.S. provisional application No. 63/410,261 filed on Sep. 27, 2022 (compound 7 with a ketal head group), each incorporated herein by reference.

Figure 14A:
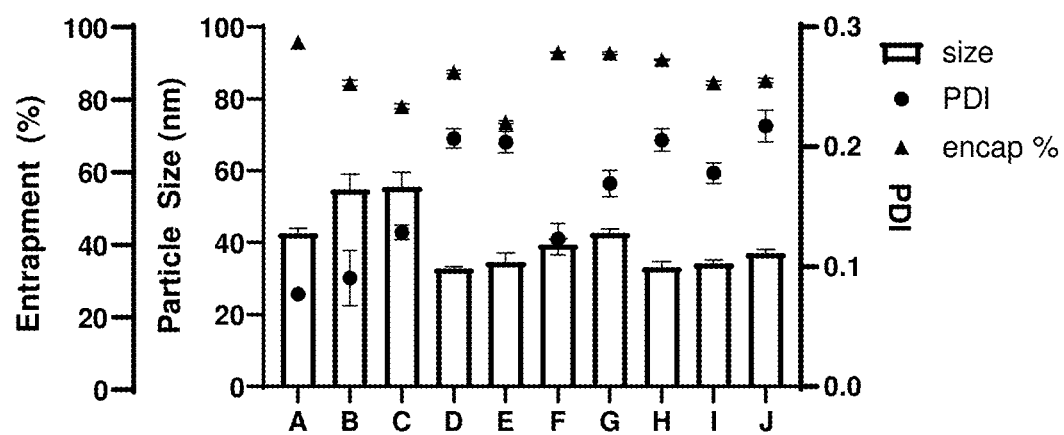
FIG. 14A shows mRNA entrapment %, particle size (nm) and polydispersity index (PDI) for Onpattro™ (LNP A); LNPs having 50 mol % of the phosphatidylcholine lipids DSPC, DOPC, POPC and DPPC (LNPs B-F); and LNPs having 40:10, 30:20, 20:30 and 10:40 mol:mol DSPC: DOPC (G-J). The LNP formulations A-J are provided in Table 7 of Example 5 and the mRNA encodes for luciferase.

The particle size and polydispersity index (PDI) of each formulation (A-J in Table 7 above) and entrapment % of mRNA are shown in FIG. 14A.

Figure 14B:
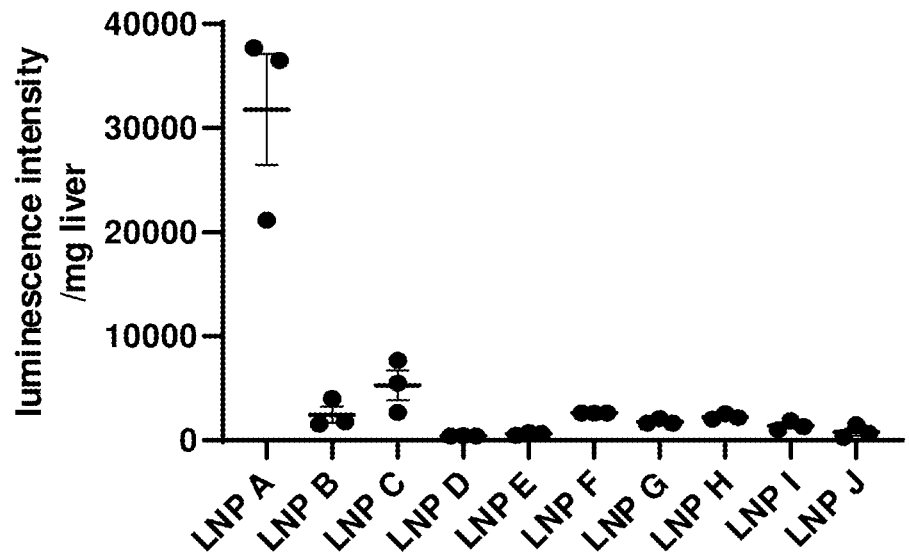
FIG. 14B shows luminescence intensity/mg liver in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.

FIG. 14B shows that the luminescence intensity/mg liver was elevated for the Onpattro™-type formulation (LNP A), while the remaining LNPs with various levels of DSPC, DOPC, POPC, DPPC at 50 mol % or combinations of DSPC and DOPC (combined content 50 mol %) were near baseline levels.

Figure 14C:
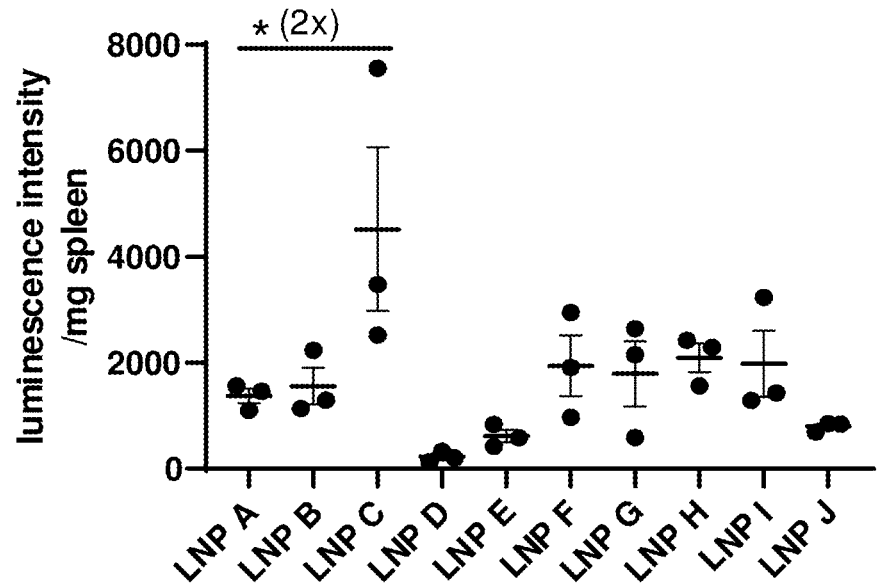
FIG. 14C shows luminescence intensity/mg spleen in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14D:
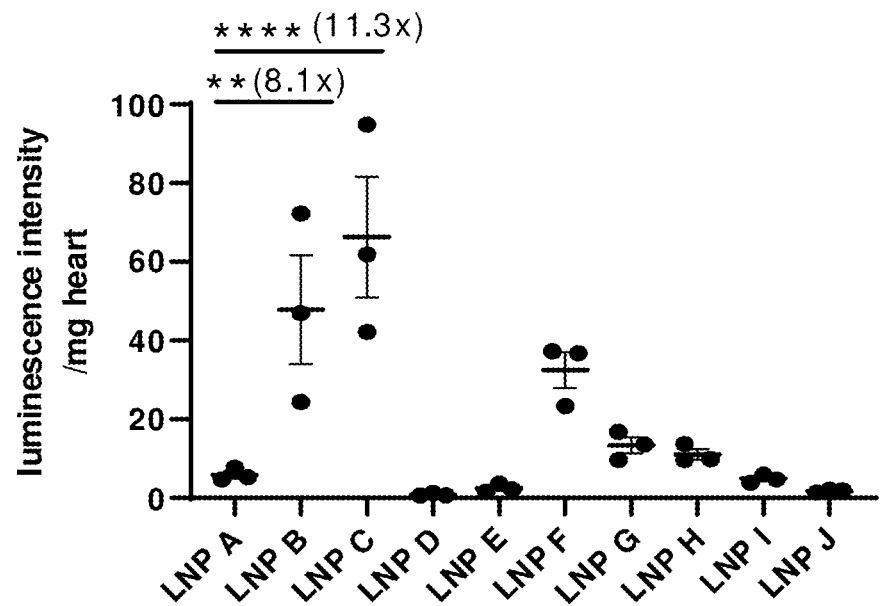
FIG. 14D shows luminescence intensity/mg heart in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14E:
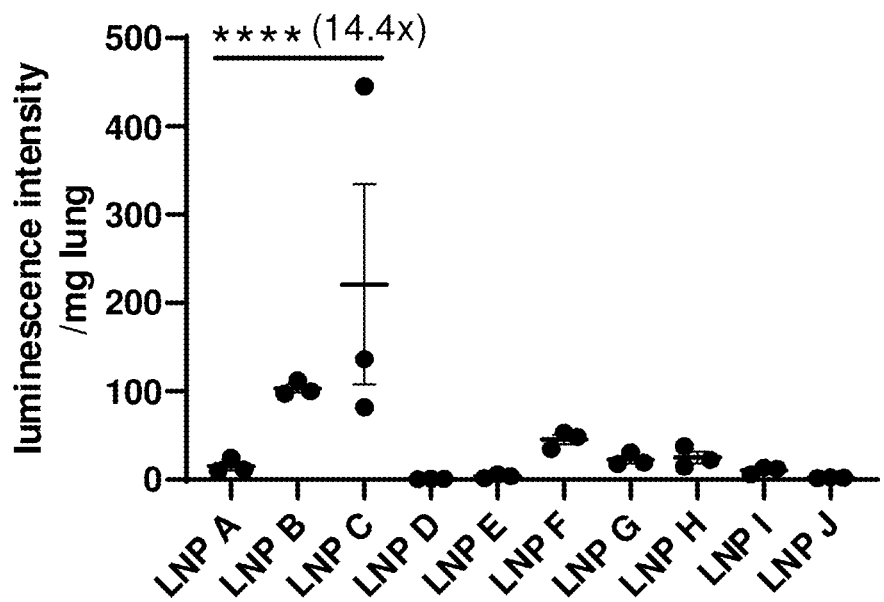
FIG. 14E shows luminescence intensity/mg lung in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14F:
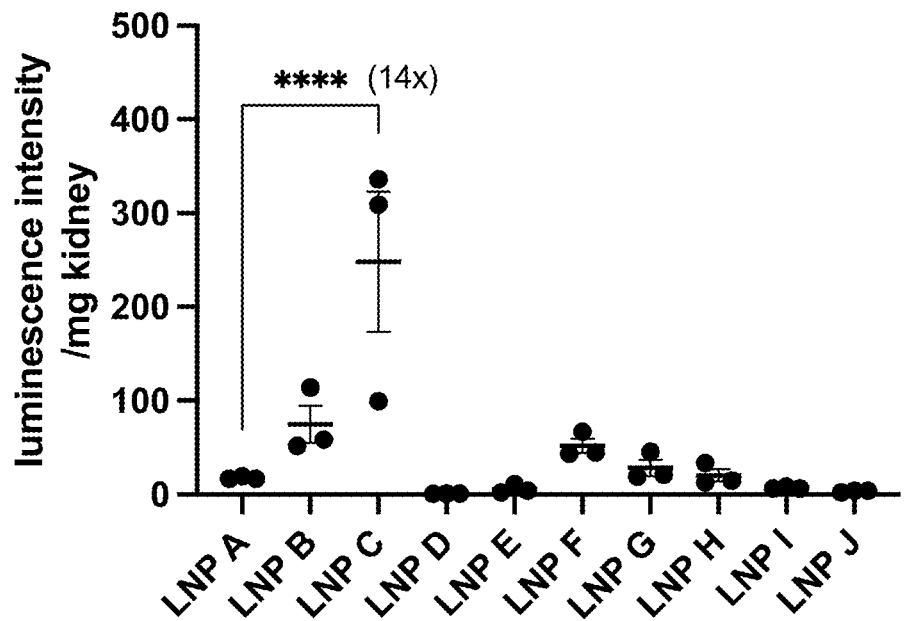
FIG. 14F shows luminescence intensity/mg kidney in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14G:
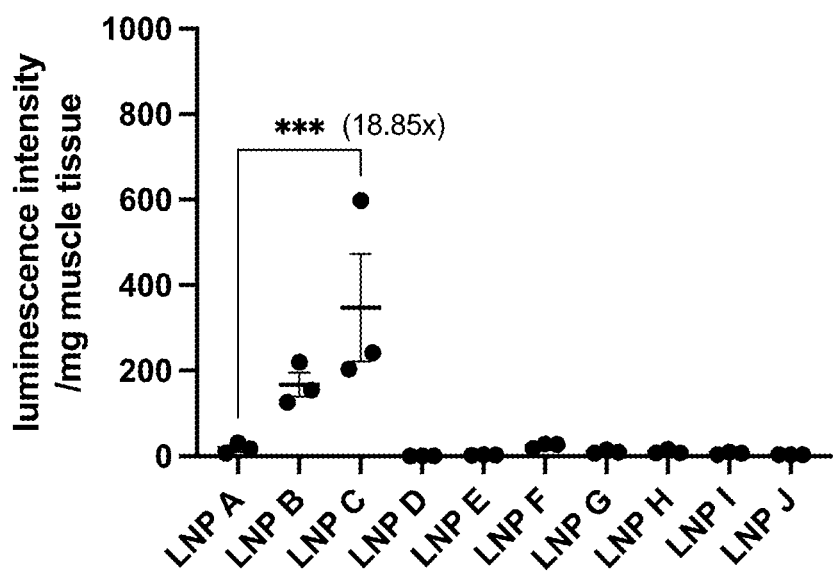
FIG. 14G shows luminescence intensity/mg muscle tissue in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14H:
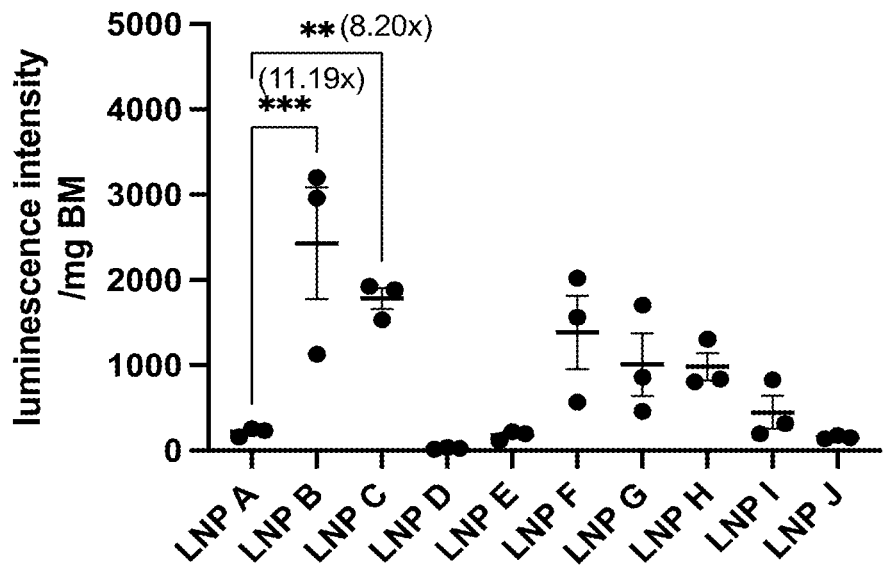
FIG. 14H shows luminescence intensity/mg bone marrow (BM) in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 14I:
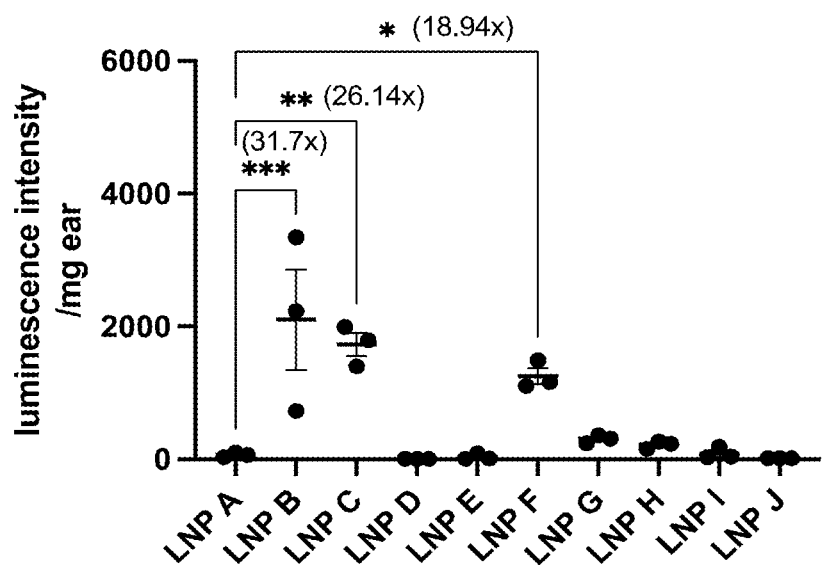
FIG. 14I shows luminescence intensity/mg ear in CD-1 mice for Onpattro™ (LNP A); LNPs having 50 mol % of the phosphatidylcholine lipids, DSPC, DOPC, POPC and DPPC (LNPs B-F); and LNPs having 40:10, 30:20, 20:30 and 10:40 mol:mol DSPC:DOPC (G-J). The LNP formulations A-J are provided in Table 7 of Example 5 and the mRNA encodes for luciferase. The mRNA expression was quantified at 24 hours post-injection by measuring luminescence.
Figure 15A:
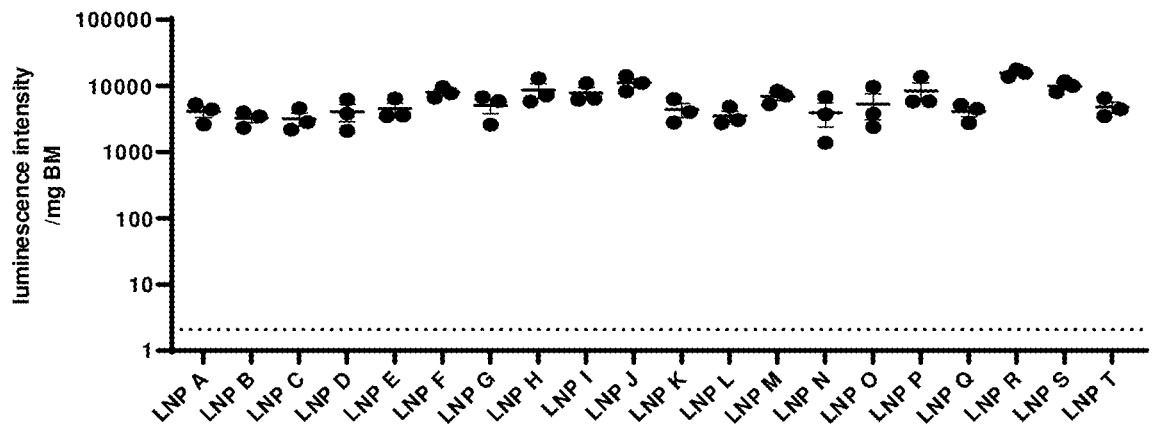
FIG. 15A shows luminescence intensity/mg bone marrow (BM) in CD-1 mice for a panel of LNPs having varying levels of DSPC and ionizable cationic lipid as indicated in Table 8 of Example 6.
Figure 15B:
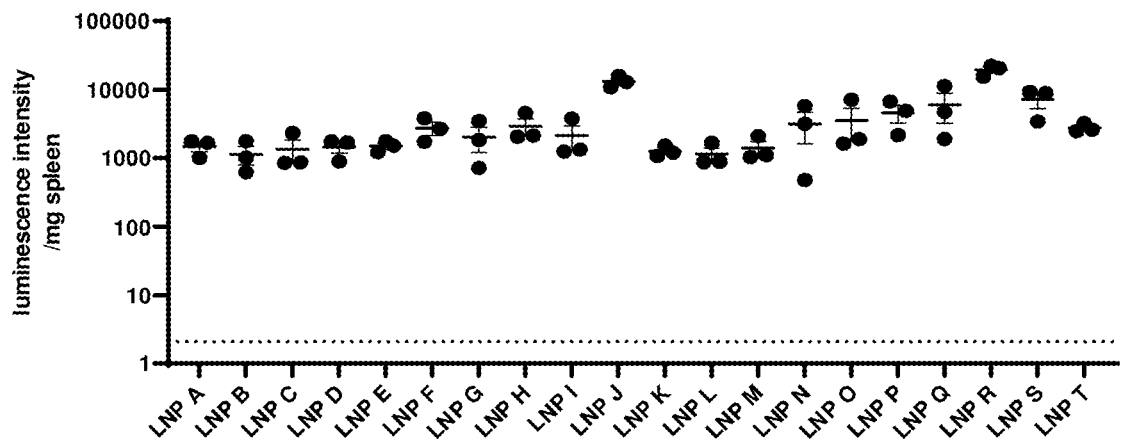
FIG. 15B shows luminescence intensity/mg spleen in CD-1 mice for a panel of LNPs having varying levels of DSPC and ionizable cationic lipid as indicated in Table 8 of Example 6.
Figure 15C:
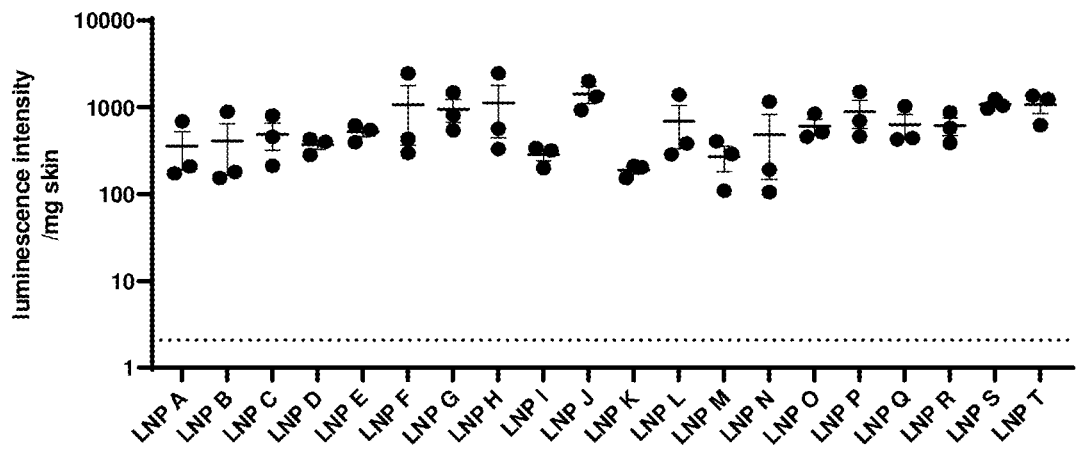
FIG. 15C shows luminescence intensity/mg skin in CD-1 mice for a panel of LNPs having varying levels of DSPC and ionizable cationic lipid as indicated in Table 8 of Example 6.
Figure 15D:
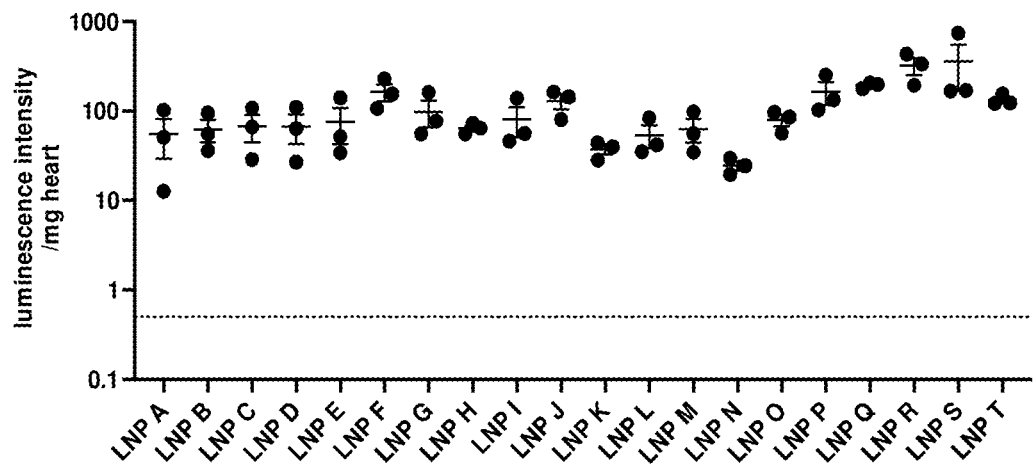
FIG. 15D shows luminescence intensity/mg heart in CD-1 mice for a panel of LNPs having varying levels of DSPC and ionizable cationic lipid as indicated in Table 8 of Example 6.
Figure 15E:
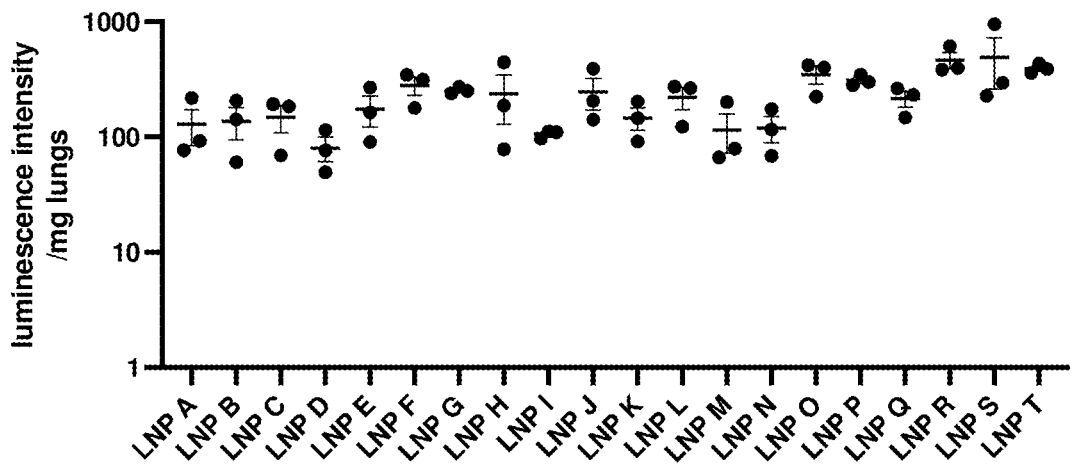
FIG. 15E shows luminescence intensity/mg lungs in CD-1 mice for a panel of LNPs having varying levels of DSPC and ionizable cationic lipid as indicated in Table 8 of Example 6.
Figure 15F:
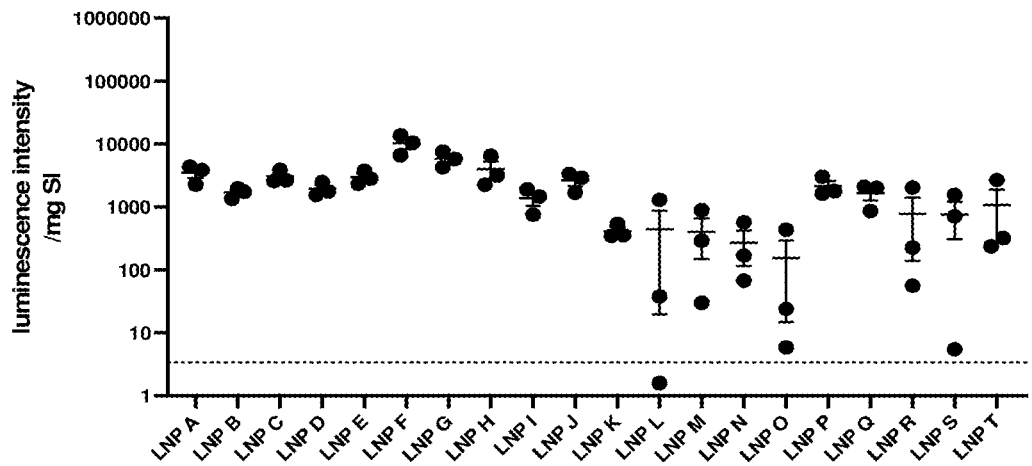
FIG. 15F shows luminescence intensity/mg small intestine in CD-1 mice for a panel of LNPs having varying levels of DSPC and ionizable cationic lipid as indicated in Table 8 of Example 6.
Figure 15G:
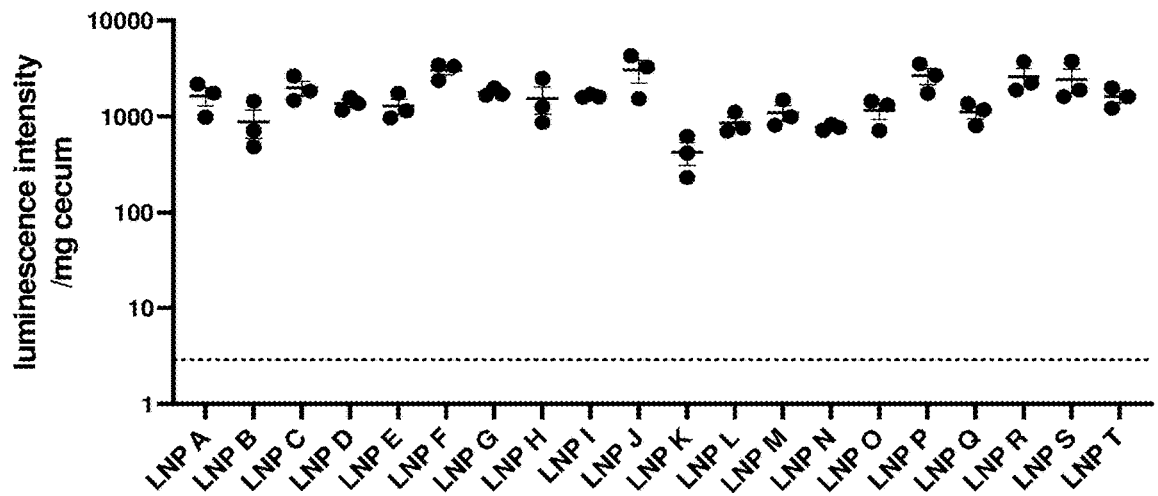
FIG. 15G shows luminescence intensity/mg cecum in CD-1 mice for a panel of LNPs having varying levels of DSPC and ionizable cationic lipid as indicated in Table 8 of Example 6.
Figure 15H:
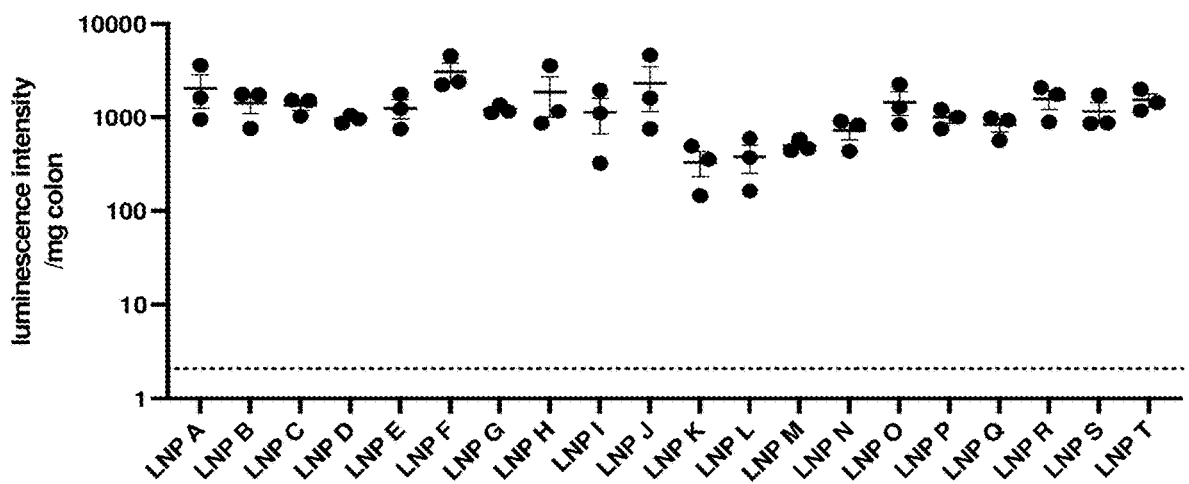
FIG. 15H shows luminescence intensity/mg colon in CD-1 mice for a panel of LNPs having varying levels of DSPC and ionizable cationic lipid as indicated in Table 8 of Example 6.

FIGS. 14C-14I show luminescence intensity/mg organ or tissue for spleen, heart, lung, kidney, muscle, bone marrow (BM) and ear at 24 hours post-injection. LNPs B and C having 50 mol % DSPC exhibited the highest luminescence intensity/mg organ or tissue relative to Onpattro™ in the extrahepatic organs/tissues, although LNP F having 50 mol % DPPC also had acceptable luminescence intensity in many of the organs/tissues examined (spleen, heart, kidney, bone marrow (BM) and ear). Dioleoylphosphatidylcholine (DOPC and POPC) LNPs (LNPs D and E) exhibited low luminescence intensity in the liver in each organ/tissue but LNPs comprising mixtures of dioleoylphosphatidylcholine (DOPC) and DSPC (LNPs G to J) exhibited elevated luminescence intensity in many of the organs/tissues that were examined in the study (see FIGS. 14C-I). These results show that LNPs with elevated levels of phosphatidylcholine lipids having saturated chains and that have a phase transition temperature above physiological temperature (DSPC and DPPC) improve delivery of mRNA beyond the liver relative those having unsaturated chains (DOPC or POPC) and possess a phase transition temperature below physiological temperature. However, combinations of phosphatidylcholine lipids with high (e.g., DSPC or DPPC) and low (e.g., DOPC or POPC) phase transition temperatures may provide improved extrahepatic delivery as well (e.g., LNPs G, H and I as shown in FIGS. 14C, 14D).

Example 6

A Variety of LNPs Having Elevated Phosphatidylcholine Content (30 mol % and Greater) and Different Ionizable Lipids Exhibit Enhanced In Vivo Extrahepatic mRNA Expression The following in vivo data demonstrate that LNPs with elevated levels of phosphatidylcholine lipid (e.g., 30-50 mol % DSPC) and formulated with a variety of different ionizable cationic lipids exhibit enhanced expression of mRNA in the bone marrow (BM), spleen, skin, heart, lungs, small intestine (SI), cecum and colon.

A panel of mRNA LNPs set forth in Table 8 with varying PC content, differing ionizable cationic lipids and N/P were prepared. The encapsulated mRNA encodes for luciferase. Tissue homogenate luciferase levels were measured in CD-1 mice as previously indicated at 24 hours post-injection.

TABLE 8

LNP panel with varying DSPC content; different ionizable cationic lipids and N/P content

| LNP | Ionizable lipid mol % | Mol % DSPC | Chol mol % | PEG-DMG mol % | N/P |
|---|---|---|---|---|---|
| A | 27.4 nMC3 | 50 | 21.1 | 1.5 | 6 |
| B | 27.4 nMC3 | 50 | 21.1 | 1.5 | 7.5 |
| C | 27.4 nMC3 | 50 | 21.1 | 1.5 | 9 |
| D | 27.4 nMC3 | 50 | 21.1 | 1.5 | 10.5 |
| E | 27.4 nMC3 | 50 | 21.1 | 1.5 | 12 |
| F | 38.5 nMC3 | 30 | 30 | 1.5 | 9 |
| G | 35.85 nMC3 | 35 | 27.65 | 1.5 | 9 |
| H | 33.05 nMC3 | 40 | 25.45 | 1.5 | 9 |
| I | 30.22 nMC3 | 45 | 23.28 | 1.5 | 9 |
| J | 27.4 C-0137 | 50 | 21.1 | 1.5 | 9 |
| K | 33 nMC3 | 50 | 32.75 | 1.5 | 9 |
| L | 29 nMC3 | 40 | 40 | 1.5 | 9 |
| M | 37.4 nMC3 | 40 | 40 | 1.5 | 9 |
| N | 45 nMC3 | 40 | 40 | 1.5 | 9 |
| O | 27.4 C-0108 | 50 | 50 | 1.5 | 9 |
| P | 27.4 C-0109 | 50 | 50 | 1.5 | 9 |
| Q | 27.4 C-0123 | 50 | 50 | 1.5 | 9 |
| R | 27.4 C-0124 | 50 | 50 | 1.5 | 9 |
| S | 27.4 C-0136 | 50 | 50 | 1.5 | 9 |
| T | 27.4 F-0023 | 50 | 50 | 1.5 | 9 |

The ionizable cationic lipids used in the panel of LNPs are set forth in Table 9 below.

TABLE 9

Ionizable cationic lipids used in the high DSPC panel of formulations

| Ionizable cationic lipid | Citation (incorporated herein by reference) |
|---|---|
| nMC3 | WO 2022/246571 |
| C108 | U.S. provisional application No. 63/410,261 filed on Sep. 27, 2022 (compound 7) |
| C109 | U.S. provisional application No. 63/410,261 filed on Sep. 27, 2022 (compound 7 with ketal head group) |
| C123 | U.S. provisional application No. 63/434,506 (compound 9) |
| C124 | U.S. provisional application No. 63/434,506 (compound 11) |
| C136 | U.S. provisional application No. 63/434,506 (compound 14) |
| C137 | U.S. provisional application No. 63/434,506 (compound 7) |
| F23 | WO2022155728A1 |

The in vivo data for tissue homogenates in liver, spleen, bone marrow (BM), abdominal skin, heart, lungs, small intestine (SI), cecum, colon for the LNP panel in Table 8 with elevated DSPC (greater than 30 mol %) are shown in FIGS. 15A-15H.

Example 7

LNPs with Elevated Phosphatidylcholine Content Have a Unique Morphology

Figure 16:
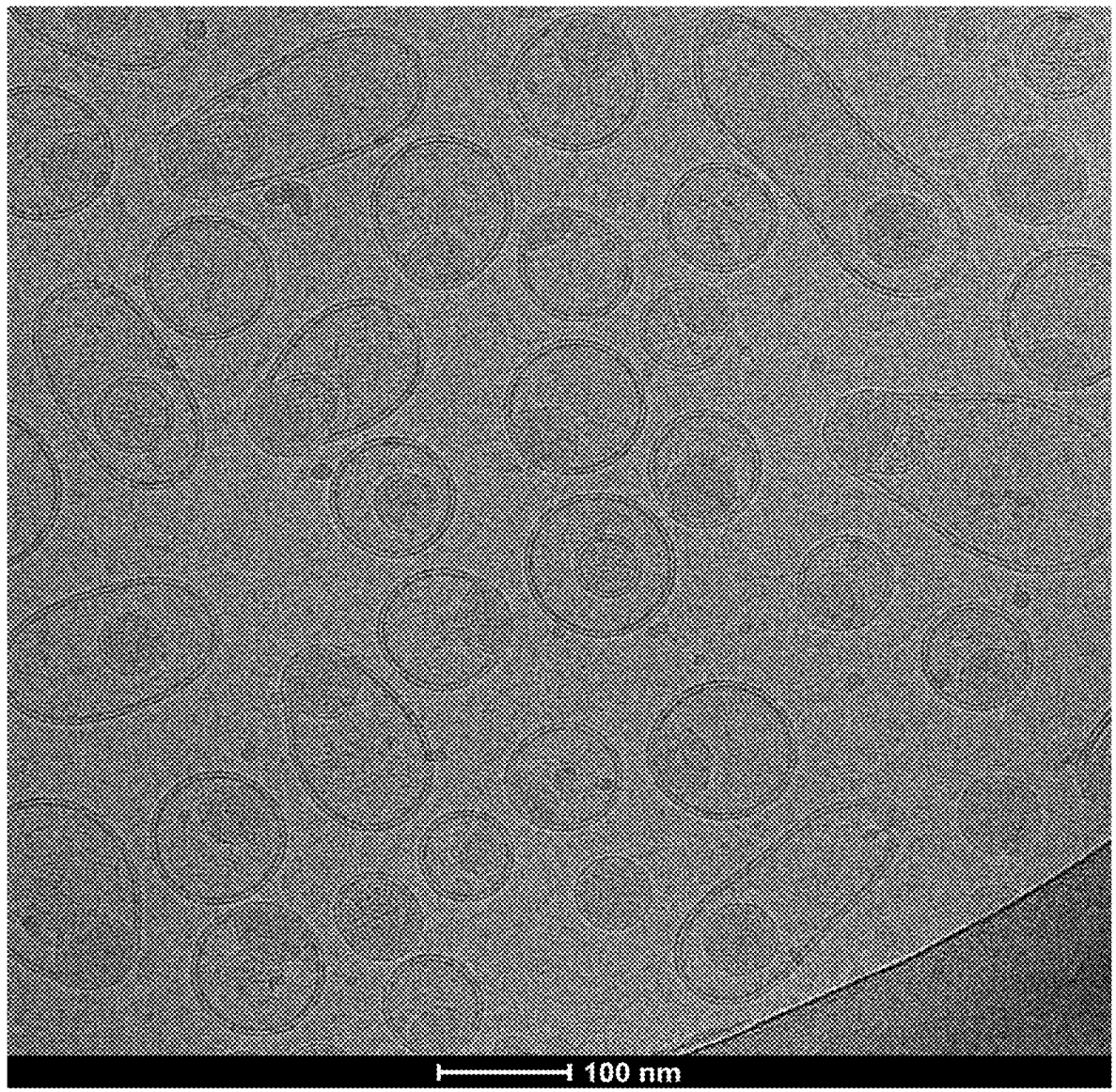
FIG. 16 shows a Cryo-TEM image of a lipid nanoparticle composed of MF019/DSPC/Chol/PEG-DMG (27.4/50/21.1/1.5 mol:mol) encapsulating mRNA encoding luciferase.

A Cryo-TEM image of a lipid nanoparticle composed of MF019/DSPC/Chol/PEG-DMG (27.4/50/21.1/1.5 mol:mol) encapsulating mRNA encoding luciferase was obtained. The image is shown in FIG. 16.

The image of the lipid nanoparticle having encapsulated mRNA with high levels of phosphatidylcholine lipid has a morphology in which there is an electron dense region that is contained within the bilayer. The core, in turn, is surrounded by a structure consistent with a lipid bilayer as shown in FIG. 16. The morphology, which is unique to LNPs having elevated phosphatidylcholine lipid, may provide the LNPs with the improved in vivo delivery properties to extrahepatic (non-liver) target sites as observed in the previous examples.

The examples are intended to illustrate the preparation of specific lipid nanoparticle mRNA preparations and properties thereof but are in no way intended to limit the scope of the invention.

The article "a" or "an" as used herein is meant to include both singular and plural, unless otherwise indicated.

The invention claimed is:

1. A pharmaceutical composition comprising a lipid nanoparticle for extrahepatic delivery of mRNA, the lipid nanoparticle comprising:
   (i) mRNA;
   (ii) a phospholipid content comprised of phosphatidylcholine lipid, the phosphatidylcholine lipid present at a lipid content of from 30 mol % to 70 mol %;
   (iii) an ionizable cationic lipid content of from 15 mol % to 45 mol %;
   (iv) a sterol selected from cholesterol or a derivative thereof; and
   (v) a hydrophilic polymer-lipid conjugate that is present at a lipid content of from 0.5 mol % to 5 mol %,
   wherein each lipid content is relative to a total lipid content of the lipid nanoparticle, the lipid nanoparticle having a pKa of between 6 and 7.5, a core in which a portion thereof is electron dense as observed by cryo-TEM, the phospholipid content has less than 5 mol % of non-phosphatidylcholine lipids and wherein the lipid nanoparticle has an N/P ratio that is between 4 and 15, wherein the pharmaceutical composition provides a prophylactic, ameliorative or a therapeutic benefit.

2. A pharmaceutical composition comprising lipid nanoparticles having encapsulated mRNA and 20 to 70 mol % of a phosphatidylcholine lipid relative to total lipid present in the lipid nanoparticles, an ionizable lipid; and at least one of a sterol and a hydrophilic polymer-lipid conjugate, the lipid nanoparticles exhibiting at least a 10% increase in gene expression of the mRNA in vivo as measured in a sub-set of cells from the bone marrow or spleen selected from macrophages, monocytes and/or T-cells at 24 hours and/or 3 days post-injection as compared to an Onpattro-type formulation of MC3/DSPC/cholesterol/PEG-lipid at 50/10/38.5/1.5, mol:mol encapsulating the mRNA, but otherwise measured under identical conditions, wherein the gene expression is quantified in an animal model by detection of cells positive for green fluorescent protein (GFP) using flow cytometry, the lipid nanoparticles bearing substantially no net charge at physiological pH and wherein at least 90% of the lipid nanoparticles have a particle size diameter between 45 and 150 nm, a core in which a portion thereof is electron dense as observed by cryo-TEM and wherein the lipid nanoparticles have an N/P ratio that is between 4 and 15, and wherein the pharmaceutical composition provides a prophylactic, ameliorative or a therapeutic benefit.

3. The pharmaceutical composition of claim 1, wherein the phosphatidylcholine lipid is distearoylphosphatidylcholine (DSPC), 1-palmitoyl-2-oleoyl-phosphatidylcholine (POPC) or dipalmitoyl-phosphatidylcholine (DPPC).

4. The pharmaceutical composition of claim 1, wherein the phosphatidylcholine lipid is distearoylphosphatidylcholine (DSPC) or dipalmitoyl-phosphatidylcholine (DPPC).

5. The pharmaceutical composition of claim 1, wherein the phosphatidylcholine lipid is a mixture of two phosphatidylcholine lipids.

6. The pharmaceutical composition of claim 5, wherein the mixture comprises distearoylphosphatidylcholine (DSPC) and dioleoylphosphatidylcholine (DOPC).

7. The pharmaceutical composition of claim 1, wherein the phosphatidylcholine lipid content is between 40 mol % and 60 mol %.

8. The pharmaceutical composition of claim 7, wherein the phosphatidylcholine lipid content is between 42 mol % and 58 mol %.

9. The pharmaceutical composition of claim 8, wherein the phosphatidylcholine lipid content is between 45 mol % and 55 mol %.

10. The pharmaceutical composition of claim 1, wherein the cationic lipid is an amino lipid.

11. The pharmaceutical composition of claim 1, wherein the ionizable, cationic lipid is present at less than 40 mol %.

12. The pharmaceutical composition of claim 1, wherein the hydrophilic polymer-lipid conjugate is a polyethyleneglycol-lipid conjugate.

13. The pharmaceutical composition of claim 1, wherein the sterol is present at from 15 mol % to 45 mol % based on the total lipid present in the lipid nanoparticle.

14. The pharmaceutical composition of claim 1, wherein the sterol is present at from 18 mol % to 40 mol % based on the total lipid present in the lipid nanoparticle.

15. The pharmaceutical composition of claim 1, wherein the lipid nanoparticle exhibits at least a 10% increase in gene expression of the mRNA in vivo as measured in a sub-set of cells from the bone marrow or spleen selected from macrophages, monocytes and/or T-cells at 24 hours and/or 3 days post-injection as compared to an Onpattro-type formulation of MC3/DSPC/cholesterol/PEG-lipid at 50/10/38.5/1.5, mol:mol encapsulating the mRNA, but otherwise measured under identical conditions, wherein the gene expression is quantified in an animal model by detection of cells positive for green fluorescent protein (GFP) using flow cytometry.

16. The pharmaceutical composition preparation of claim 2, wherein the green fluorescent protein is measured in a macrophage/monocyte cell population isolated from the spleen or liver of the mouse post-injection and wherein the increase in expression is determined by measuring a percentage of cells in the cell population that are positive for the eGFP.

17. The pharmaceutical composition of claim 15, wherein the green fluorescent protein is measured in a macrophage/monocyte cell population isolated from the spleen or liver of the mouse post-injection and wherein the increase in expression is determined by measuring a percentage of cells in the cell population that are positive for the eGFP.

18. The pharmaceutical composition of claim 17, wherein the green fluorescent protein is measured 3 days post-injection and wherein the animal model is a mouse.

19. The pharmaceutical composition of claim 15, wherein the in vivo expression of green fluorescent protein in a macrophage/monocyte cell population isolated from the bone marrow or spleen of the mouse post injection is increased by at least 50% over a sphingomyelin-containing LNP that substitutes sphingomyelin for the DSPC but otherwise has an identical lipid composition as the lipid nanoparticle.

20. The pharmaceutical composition of claim 1, wherein the lipid nanoparticle exhibits at least a 10% increase in gene expression of the mRNA in vivo as measured in an extrahepatic tissue or organ.

21. The pharmaceutical composition of claim 1, wherein the extrahepatic tissue or organ is spleen, bone marrow, lungs, kidney, heart, abdominal skin, back skin and/or ear.

22. The pharmaceutical composition of claim 1, wherein the lipid nanoparticle has 0.5 to 2.5 mol % hydrophilic polymer lipid conjugate.

23. The pharmaceutical composition of claim 2, wherein the lipid nanoparticles in the preparation have 0 to 2.5 mol % hydrophilic polymer lipid conjugate.

24. A pharmaceutical composition comprising a lipid nanoparticle comprising encapsulated mRNA and 35 to 60 mol % of a phospholipid content that is a phosphatidylcholine lipid, an ionizable amino lipid present at between 15 and 45 mol %; and a sterol present at between 15 and 45 mol %, each mol % being measured relative to a total lipid content of the nanoparticle, the lipid nanoparticle having a core, wherein a portion of the core has an electron dense region as observed by cryo-TEM, and wherein the lipid nanoparticle has a pKa of between 6 and 7.5, is neutral at physiological pH and has an N/P ratio that is between 4 and 15 and a size that is between 45 and 150 nm in diameter, the phospholipid content having less than 5 mol % of non-phosphatidylcholine lipids, and wherein the pharmaceutical composition provides a prophylactic, ameliorative or a therapeutic benefit.

25. The pharmaceutical composition of claim 24, wherein the sterol is cholesterol.

26. The pharmaceutical composition of claim 24, wherein a hydrophilic polymer-lipid conjugate is present at 0 to 2.5 mol %.

27. The pharmaceutical composition of claim 24, wherein the hydrophilic polymer-lipid conjugate is present at 0 to 2.0 mol %.

28. The pharmaceutical composition of claim 24, wherein the phosphatidylcholine lipid is or comprises distearoylphosphatidylcholine (DSPC).

29. The pharmaceutical composition of claim 24, wherein a polydispersity index (PDI) of the particle is less than 0.20.

30. The pharmaceutical composition preparation of claim 2, wherein the lipid nanoparticles have a polydispersity index (PDI) of less than 0.20.

* * * * *